(12) United States Patent
Houben et al.

(10) Patent No.: US 6,572,542 B1
(45) Date of Patent: Jun. 3, 2003

(54) SYSTEM AND METHOD FOR MONITORING AND CONTROLLING THE GLYCEMIC STATE OF A PATIENT

(75) Inventors: Richard Houben, Berg en Terblijt (NL); Vincent Larik, Kerkrade (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/518,796

(22) Filed: Mar. 3, 2000

(51) Int. Cl.[7] .............................. A61B 5/00; A61B 5/04; A61B 5/02; A61B 10/00
(52) U.S. Cl. ...................... 600/300; 600/544; 600/508; 600/365; 128/920; 128/925
(58) Field of Search .................. 706/924; 705/2–3; 600/300, 301, 345–365, 544–545; 604/66; 128/920–925

(56) References Cited

U.S. PATENT DOCUMENTS

| | | | |
|---|---|---|---|
| 3,877,873 A | | 4/1975 | Winitz |
| 4,408,905 A | | 10/1983 | Ehrenkranz |
| 5,741,211 A | * | 4/1998 | Renirie et al. ............... 600/300 |
| 5,844,862 A | | 12/1998 | Cocatre-Zilgien |
| 5,919,216 A | | 7/1999 | Houben et al. |
| 6,067,467 A | * | 5/2000 | John ........................... 600/544 |

OTHER PUBLICATIONS

"Detection of Spikes with Artificial Neural Networks Using Raw EEG" Özdamar et al., Computers and Biomedical Research 31, 1998, pp. 122–142.
"Monitoring Set–Up for Selection of Parameters for Detection of Hypoglycaemia in Diabetic Patients" Heger et al., Medical and Biological Engineering & Computing, Jan. 1996, pp. 69–75.
"The Relationship Between Glucose Metabolic Processes and the ECG" Houben et al., Medtronic Science and Technology Journal, Summer 1997, pp. 36–41.

* cited by examiner

Primary Examiner—Max F. Hindenburg
Assistant Examiner—Michael Astorino
(74) Attorney, Agent, or Firm—Thomas F. Woods; Eric R. Waldkoetter; Tom G. Berry

(57) ABSTRACT

Information derived from ECG signals and EEG signals may be employed in combination to reliably predict the onset, or to indicate the presence of, hypoglycemia in a human patient. In one embodiment, ECG and EEG signals are processed and the information derived from them is combined to determine whether a patient suffering from diabetes is undergoing a hypoglycemic event, or whether such an event is imminent. Input data from the patient or a health care provider may also be used to increase the accuracy and reliability of the system. Detection of a hypoglycemic event by the system can result in the output of an alarm signal and/or the delivery or administration of a beneficial agent such as insulin, glucagon or diazoxide to the patient. The system may be implantable, external, or a combination of external and implantable components. The control strategy of the present system is preferably microprocessor based and/or implemented using dedicated electronics. In another embodiment, the glycemic state of the patient is continuously or relatively continuously monitored and controlled by the system. The system may contain any of a number of different types of feedback control systems for monitoring the glycemic state of a patient and controlling same, such as fuzzy logic systems, adaptive systems, reinforcement learning systems, and the like.

94 Claims, 14 Drawing Sheets

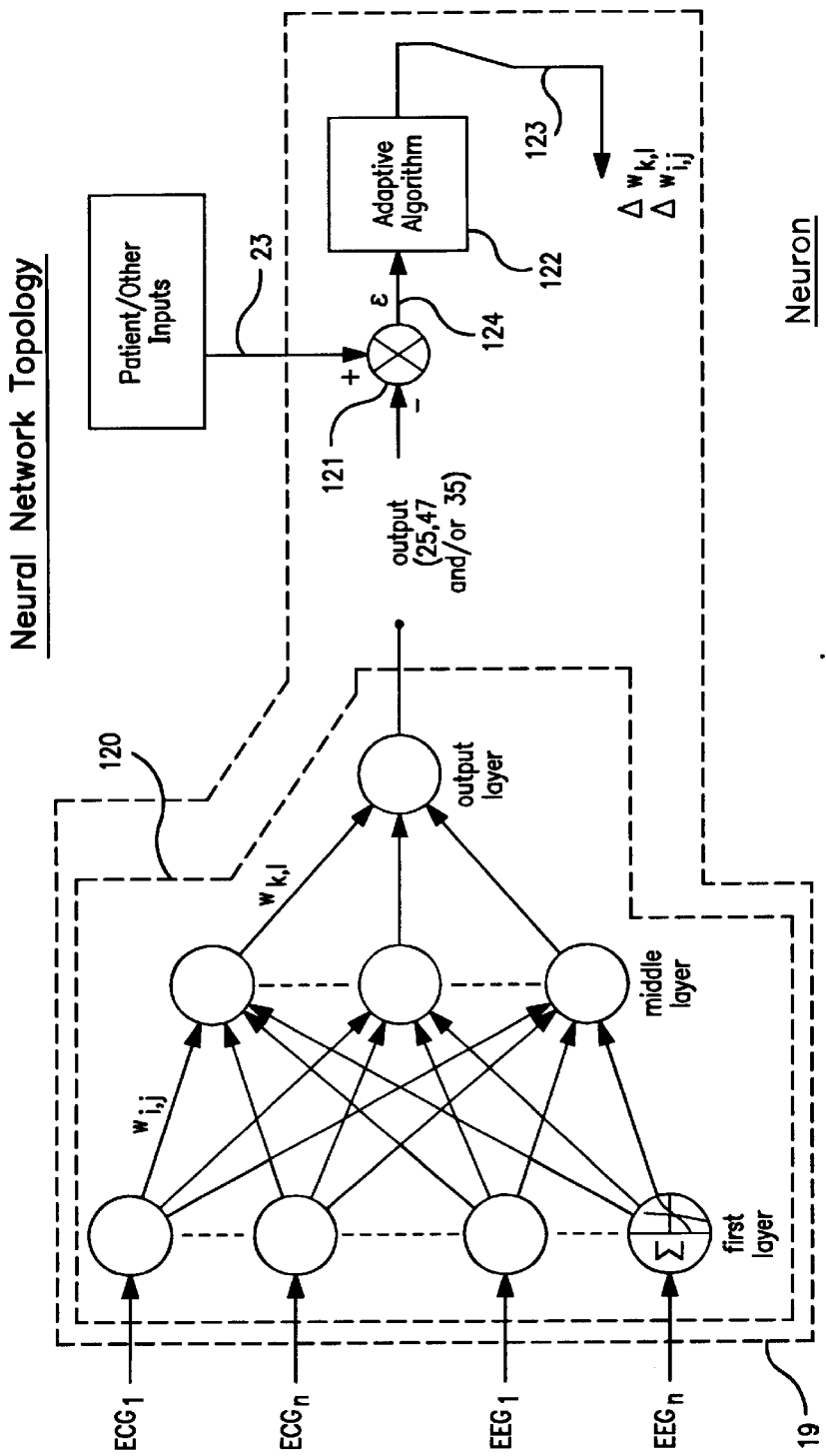
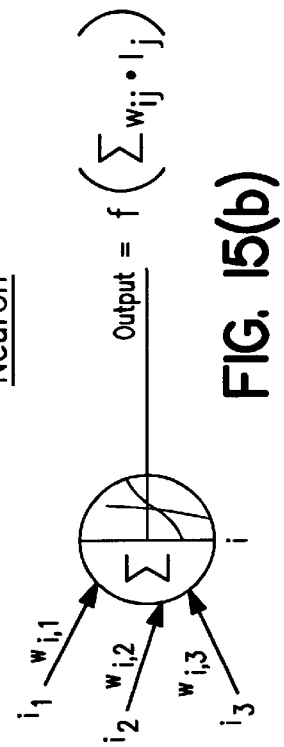
FIG. 15(a)
FIG. 15(b)

SYSTEM AND METHOD FOR MONITORING AND CONTROLLING THE GLYCEMIC STATE OF A PATIENT

FIELD OF THE INVENTION

This application relates to a system and method for monitoring and/or controlling patient diabetes-related blood constituents.

BACKGROUND OF THE INVENTION

The number of diabetes mellitus (DM) patients in the U.S. in 1993 was estimated to be 7.8 million persons (roughly 3.4% of the total US population). The number of patients with diabetes mellitus has steadily grown over the last 25 years (Diabetes 1996: Vital Statistics. American Diabetes Association Inc., 1996). See FIG. 1 (U.S. Diabetes Mellitus prevalence data 1993 adapted from Diabetes Vital Statistics, American Diabetes Association 1993).

From this total, 10% (or about 0.8 million persons) are estimated to be insulin dependent diabetes mellitus (IDDM) patients. The Diabetes Control and Complications Trial (the DCCT) showed a 70% reduction in complications resulting from tight metabolic control in IDDM patients. See "The effect of intensive treatment of diabetes on the development and progression of long-term complications in insulin-dependent diabetes mellitus", The Diabetes Control and Complications Trial Research Group, The New England Journal of Medicine, Vol. 329, No 14. Sep. 30, 1993. The DCCT underscores the importance of developing a better way to control blood glucose for the IDDM patient group. Unfortunately, the study showed substantial evidence that the frequency of hypoglycemic excursions increases 2–3 times in IDDM patients subjected to tight metabolic control compared to regular treatment. Frequent hypoglycemic excursions additionally create hypoglycemic unawareness, a state where patients become incapable of recognizing themselves the usual symptoms associated with hypoglycemia.

In the U.S. diabetes mellitus (DM) population, 90% (or 7 million persons) are estimated to be non-insulin dependent diabetes mellitus (NIDDM) patients. NIDDM patients may be subdivided into insulin users (30%, or 2.3 million persons), of which at least 25% (or 0.52 million persons) measures their blood glucose levels on a daily basis. The percentage of NIDDM patients receiving insulin treatment increases with the duration of NIDDM from 25% (0–4 years) to 60% (>20 years). It is estimated that the diagnosed number of NIDDM patients reflects only about 50% of the actual population suffering from NIDDM. However, it is recognized that only a limited percentage of this group requires improved treatment. The remainder of the NIDDM population generally self manages the disease though careful meal planning and exercise, or by means of oral hypoglycemic agents.

Comprehensive diets and injective insulin administration, combined with glucose level determination multiple times a day, may provide an acceptable degree of metabolic control, but often fall short of being optimum and may also induce considerable patient discomfort. Injected insulin does not enter the circulation directly, resulting in a delayed and reduced effect in bringing plasma glucose level down to acceptable values. Increased and prolonged hyperglycemic and/or hypoglycemic periods contribute to chronic complications. Ocular complications such as cataracts and retinopathy occur in approximately 50% of such patients after ten years. Severe nephropathy, neuropathy, and gangrene of the feet and skin complications are frequently observed.

Hypoglycemic medication, such as the sulfonylureas class of drugs, directly potentiate the release of insulin from vital pancreatic beta-cells. Severe hypoglycemia is frequently reported as a side effect of this type of drugs. More recent families of hypoglycemic agents such as biguanides and acarbose reduce the hypoglycemic threat but have a limited therapeutic scope and have undesirable side effects, which include nausea, abdominal pain and diarrhea.

A relationship between diabetes mellitus and coronary heart disease has long been suggested. See Garcia, M. J. et al., "Morbidity and Morality in Diabetics in the Framingham Population: Sixteen Year Follow-Up Study," *Diabetes,* 23:105–11 (1974); Fein, F. S., "Heart Disease In Diabetes," Cardiovasc. *Rev. Rep.,* 3:877–93 (1982); "Relationship of Glucose Tolerance to Prevalence of ECG Abnormalities and to Annual Mortality From Cardiovascular Disease: Results of the Paris Prospective Study," Ducimetiere et al.,*J. Chron. Dis.,* Vol. 32, pp. 759 to 766 (1979). Additionally, a correlation between a patient's ECG and blood potassium levels, and variations in the ECG following introductions of insulin, have been recognized. See Heine et al., *Acta Endocrinologica* 1984, 106:241–247.

The field of glucose monitoring is active. Its importance lies in indicating to the diabetic when and how much insulin should be taken. Ideally, glucose monitoring would be continuous and non-invasive. With an accurate continuously monitoring glucose sensor, information would constantly be available, either to signal a condition of hyperglycemia or hypoglycemia, or even direct and enable a closed loop system by which insulin would be automatically delivered so as to keep glucose levels close to normal physiological levels. Such a system would reduce chronic complications and provide an obvious increase in quality of life for IDDM patients.

A closed loop control system driven by a glucose sensor would enable the delivery of accurate amounts of insulin, keeping glucose levels near physiological levels while constantly monitoring upcoming hypoglycemic hazards. The key component missing in such a system is a reliable, accurate and biocompatible glucose sensor. Compared to the IDDM population, the NIDDM population is very heterogeneous in age, therapy, and stage of the disease.

Most glucose sensors presently in common use are based on electrochemical methods such as the electro-enzymatic method where blood glucose is oxidized under glucose-oxidase control, producing gluconic acid and hydrogen peroxide. By using this enzymatic reaction as a first stage, the problem is reduced to a measurement of used oxygen or produced hydrogen peroxide (i.e., the amperometric method). Alternately, the produced gluconic acid can be determined directly (i.e., the potentiometric method). Both sensor types suffer from stability problems, however. Optical glucose sensors have been experimented with, but for several reasons are not feasible for long term continuous monitoring, and especially not for implantable glucose monitoring applications.

Patents and printed publications describing various aspects of the foregoing problems and the state of the art are listed below.

U.S. Pat. No. 3,877,873 entitled "Test for Metabolic Conditions in Blood or Serum" to Winitz U.S. Pat. No. 4,408,905 entitled "Urinary Temperature Measurement Device" to Ehrenkranz.

U.S. Pat. No. 4,476,901 entitled "Apparatus for Improving Blood Sugar Control in Diabetics" to Kraegen et al.

U.S. Pat. No. 4,776,842 entitled "Device for the Administration of Medications" to Franetzki et al.

U.S. Pat. No. 4,731,051 entitled "Programmable Control Means for Providing Safe and Controlled medication Infusion" to Fischell.

U.S. Pat. No. 4,871,351 entitled "Implantable Medication Infusion System" to Feingold.

U.S. Pat. No. 5,190,041 entitled "System for Monitoring and Controlling Blood Glucose" to Palti.

U.S. Pat. No. 5,231,988 entitled "Treatment of Endocrine Disorders by Nerve Stimulation" to Wernicke.

U.S. Pat. No. 5,368,028 entitled "System for Monitoring and Controlling Blood and Tissue Constituent Levels" to Palti.

U.S. Pat. No. 5,540,734 entitled "Cranial Nerve Stimulation Treatments Using Neurocyberetic Prostheses" to Zabara.

U.S. Pat. No. 5,741,211 entitled "System and Method for Continuous Monitoring of Diabetes-related Blood Constituents" to Renirie et al.

U.S. Pat. No. 5,844,862 entitled "Skin Temperature Radio Telemetry and Alarms" to Cocatre-Zilgien.

U.S. Pat. No. 5,919,216 entitled "System and Method for Enhancement of Glucose Production by Stimulation of Pancreatic Beta Cells" to Houben et al.

Alvestrand, A., Wahren, J., Smith, D., and DeFronzo, R. A. Insulin-mediated potassium uptake is normal in uremic and healthy subjects. Am. *J.Physiol.* 246:E174–80, 1984.

Anderson, E. A., Hoffman, R. P., Balon, T. W., Sinkey, C. A. and Mark, A. L. (1991) Hyperinsulinemia produces both sympathetic neural activation and vasodilation in normal humans. *J. Clin. Invest.* 87, pp. 2246–2252.

Berne, C., Fagius, J. and Niklasson, F. (1989) Sympathetic response to oral carbohydrate administration. Evidence from microelectrode nerve recordings. *J. Clin. Invest.* 84, pp. 1403–1409.

Berne, C. and Fagius, J. (1993) Metabolic regulation of sympathetic nervous system activity: lessons from intraneural nerve recording. International Journal of Obesity 17 (suppl 3), S2–S6.

Dear H D, Buncher C R, Sawayama T. (1969) Changes in electrocardiogram and serum potassium values following glucose ingestion. *Arch Internal Medicine* 124, pp. 25–28.

DeFronzo R A, Felig P, Ferrannini E, Wahren J, Effect of graded doses of Insulin on splanchic and peripheral potassium metabolism in man. *Am. J. of Physiol.* 238 (Endocrin. Metab. 1): E421–27, 1980

Frandsen, H., Fagius, J., Nikklasson, F., (1990) Muscle sympathetic nerve response after oral glucose is attenuated in type I diabetes. *Diabetologica* 33, A165.

Heinemann L, Meinhold J, Kunze W. (1995) Hypoglycemia detection be ECG recording?. *Diabetes Care* 18 no 1, p139–140.

Heger G; Howorka K; Thoma H; Tribl G; Zeitlhofer J (1996) Monitoring set-up for selection of parameters for detection of hypoglycaemia in diabetic patients, *J Med Biol Eng Comput*, January 1996, 34:1, 69–75

Howorka K; Heger G; Schabmann A; Anderer P; Tribl G; Zeitlhofer J (1996) Severe hypoglycaemia unawareness is associated with an early decrease in vigilance during hypoglycaemia, *Psychoneuroendocrinology*, Apr, 21:3, 295–312

Joslin's Diabetes Mellitus, thirteenth edition, Gordon Weir, Ronald Kahn, 1994, ISBN 0-8121-1531-7

Katz, A. M., Physiology of the Heart, Raven Press, New York 1977.

Kern, W., Schlosser, C., Kerner, W., Pietrowsky, R., Born, J. and Fehm, H. L. (1994) Evidence for effects of insulin on sensory processing in humans. *Diabetes* 43, 351–356.

Kreagen, E W., Chisholm D J, (1988) Closure of the loop by glucose sensing, Physiological and practical considerations. Implantable glucose sensors, The State of the Art International Symposium Reisenburgt. *Hormone and Metabolic Research* Vol. 20, 1–4

Marques J L; George E; Peacey S R; Harris N D; Macdonald I A; Cochrane T; Heller S R (1997) Altered ventricular repolarization during hypoglycaemia in patients with diabetes, *Diabet Med*, 14:8, 648–54

Minaker-K L; Meneilly-G S; Flier-J S; Rowe-J W, Insulin-mediated hypokalemia and paralysis in familial hypokalemic periodic paralysis. *Am J. of Med.* June 1988; 84(6): 1001–6

Ostrander L D, Weinstein B J. (1964) Electrocardiographich changes after glucose ingestion. *Circulation* 30, pp. 67–76.

Parrish A E, Sugar S J, Fazekas J F. (1952) A relationship between electrocardiographich changes and hypokalemia in insulin-induced hypoglycemia. *American Heart Journal*. pp. 815–821.

Petersen K G, Schluter K J, Kerp L. (1982) Regulation of serum potassium during insulin-induced hypoglycemia. *Diabetes* 31, pp. 615–617.

Rowe, J. W., Young, J. B., Minaker, K. L., Stevens, A. L., Pallotta, J. and Landsberg, L. (1981) Effect of insulin and glucose infusions on sympathetic nervous system activity in normal man. *Diabetes* 30, 219–225.

Riley C P, Oberman A, Sheffield L T (1972) Electrographic effects of glucose ingestion. *Arch Internal Medicine* 130 pp.703–707.

Spraul, M., Anderson, E. A., Bogardus, C. and Ravussin, E. (1994) Muscle sympathetic nerve activity in response to glucose ingestion. Impact of plasma insulin and body fat. *Diabetes* 43, 191–196.

Teagtmeyer H, Russel R R III, Biochemistry of the heart, Current concepts in cardiovascular physiology 2–61

Tribl G; Howorka K; Heger G; Anderer P; Thoma H; Zeitlhofer J (1996) EEG topography during insulin-induced hypoglycemia in patients with insulin-dependent diabetes mellitus, *Eur Neurol*, 36:5, 303–9.

Zierler K, Rogus E M. (1980) Hyperpolarization as a mediator of insulin action: increased muscle glucose uptake induced electrically. *American Journal of Physiology* 239 (Endocrine metabolism 2) pp. E21–29.

Zierler K., Rogus E M. (1981) Rapid hyperpolarization of rat skeletal muscle induced by insulin. *Biochimica et Biophysica Acta* 640, 687–692.

Zierler K., Rogus E M, Scherer R W, Wu FS. (1985) Insulin action on the membrane potential and glucose uptake: Effects of high potassium. *Am. Journal of Physiology* 249: E17–25.

All patents and printed publications listed hereinabove are hereby incorporated by reference herein, each in its respective entirety. As those of ordinary skill in the art will appreciate readily upon reading the Summary of the Invention, Detailed Description of the Preferred Embodiments and Claims set forth below, at least some of the devices and methods disclosed in the patents and publications listed hereinabove may be modified advantageously in accordance with the teachings of the present invention.

It will now be seen that there exists a need for a system capable of continuously monitoring blood constituents from which patient insulin or other beneficial agent need may be determined, a system capable of determining and indicating such a need, and a system capable of automatically delivering at least one beneficial agent in response to such a determination or indication and/or alerting the patient that a dangerous situation may be developing. There further exists a need for a system capable of quickly, reliably and accurately determining that a hypoglycemic state exists in a patient. Finally, there exists a need for a system capable quickly, reliably and accurately determining that the onset of a hypoglycemic state in the patient is imminent, and alerting the patient, a health care giver or emergency service of same.

SUMMARY OF THE INVENTION

The present invention has certain objects. That is, the present invention provides solutions to problems existing in the prior art. It is an object of the present invention to provide a system and method for continuous sensing of hypo- or hyper-glycemic state, the rate of change of blood glucose levels in respect of time, and/or blood insulin and/or blood glucose levels, the system being wearable by a patient or implantable therein. Another object of the present invention is to provide a sensor which is capable of detecting changes in blood insulin and/or glucose based upon the processing of ECG and EEG signals, and which provides a reliable correlation between monitored ECG and EEG parameters and insulin and/or glucose levels.

Various embodiments of the present invention have advantages, including one or more of the following: (a) improving the degree of direct or indirect control that may be exercised over the blood glucose and/or insulin levels of a diabetic patient; (b) providing timely notification to a patient or health care provider that the patient is about to enter or has entered into a hypoglycemic state; (c) providing timely notification to a patient or health care provider that the patient is about to enter or has entered into a hyperglycemic state; (d) quickly delivering a beneficial agent to a patient before a hypoglycemic or hyperglycemic state develops or becomes dangerous; (e) continuously updating and adapting its control program so that more reliable and accurate predictions of a hypoglycemic and/or hyperglycemic state may be made; (f) increased accuracy in the detection and prediction of a hypoglycemic and/or hyperglycemic state; (g) overcoming the deficiencies of relying on ECG or blood glucose data alone when detecting the presence or onset of a hypoglycemic state and/or a hyperglycemic state; (h) increasing patient safety and lowering health care costs owing to better control of patient blood glucose and/or insulin levels.

Various embodiments of the system of the present invention have certain features. We discovered that information derived from ECG signals and EEG signals may be successfully employed in combination to reliably predict the onset, or to indicate the presence of, hypoglycemia. Direct or indirect monitoring of blood glucose levels may additionally be employed to detect hyperglycemia, and in response to detection of a hyperglycemic state output an alarm signal or cause insulin to be delivered to the patient.

In one system of the present invention, ECG and EEG signals are processed and the information derived from them is combined to determine whether a patient suffering from diabetes is undergoing a hypoglycemic event, or whether such an event is imminent. Input data from the patient, a health care provider or one or more sensors may also be used to increase the accuracy and reliability of the system. Detection of a hypoglycemic or hyperglycemic event by the system can result in an alarm signal being output, and the delivery or administration of a beneficial agent such as insulin, glucagon or diazoxide. The system may be implantable, external, or a combination of external and implantable components. The control strategy of the present system is preferably microprocessor based and/or implemented using dedicated electronics.

Alternatively, the present invention may comprise an open loop control system in which the delivery of a beneficial agent to the patient in response to an alarm signal being generated is not feedback controlled by an on-line insulin level determination, for example. In an open loop system of the present system insulin or other beneficial agent delivery is based on a predetermined or preprogrammed schedule. It has been established that in a healthy person, the insulin levels are elevated even before the blood glucose level rises, due to neural factors and the involvement of gut hormone levels. During meal periods, open loop systems perform better than closed loop systems, due to the capability of starting the insulin rate increase during and even before meal ingestion. Accordingly, it is anticipated that the invention may be adapted to a system which is closed loop controlled generally, but open loop controlled in accordance either with a programmed time schedule, or in response to external programming by the patient.

The hypoglycemic and/or hyperglycemic alarms and feedback control systems of the present invention are capable of providing enhanced control of diabetes, leading to a reduction in the chronic complications of DM by as much as 70% (as indicated by the Diabetes Control and Complications Trial or DCCT, 1993). The DCCT study revealed that intensified insulin treatment decreased $HbA_{1c}$ levels by at least 2% and also subsequently reduced long-term microvascular complications by at least 70%, in comparison to standard treatment techniques.

Those favorable results were accomplished, however, at the cost of a twofold increase in mostly nocturnal hypoglycemic excursions, as well as increased incidence of hypoglycemic unawareness. The DCCT studies thus indicated that DM patients subjected to intensified insulin treatment were sub-optimally controlled. Later studies by Colwell (1994) and Wolffenbuttel (1995) provided similar results for NIDDM patients, where changes in medical care were found to be directly related to the improvement of $HbA_{1c}$ levels below 6% as a result of intensified insulin treatment. Nevertheless, and as discussed above, continuous detection of hypoglycemic threat remains an unmet clinical need.

Optimal control of patients implies reducing the long term threats of microvascular complications and nocturnal hypoglycemic events. The system of the present invention satisfies those long felt but unmet needs by providing a reliable hypoglycemia detection system that permits enhanced, tight control of blood glucose levels, and thereby reduces the risk of hypoglycemic coma within acceptable limits. Various embodiments of the system of the present invention are also capable of detecting a hyperglycemic state and responding to same (e.g., output of alarm signal or delivery of one or more beneficial agents).

Other objects, features, advantages and embodiments of the present invention will become apparent upon reading the Detailed Description of the Preferred Embodiments and the Claims.

BRIEF DESCRIPTION OF THE DRAWINGS

FIG. 15(a) shows one neural network embodiment of processor 19 of the present invention;

FIG. 15(b) shows one processing node of the neural network of FIG. 15(a), and

DETAILED DESCRIPTION OF THE PREFERRED EMBODIMENTS

Figure 1:
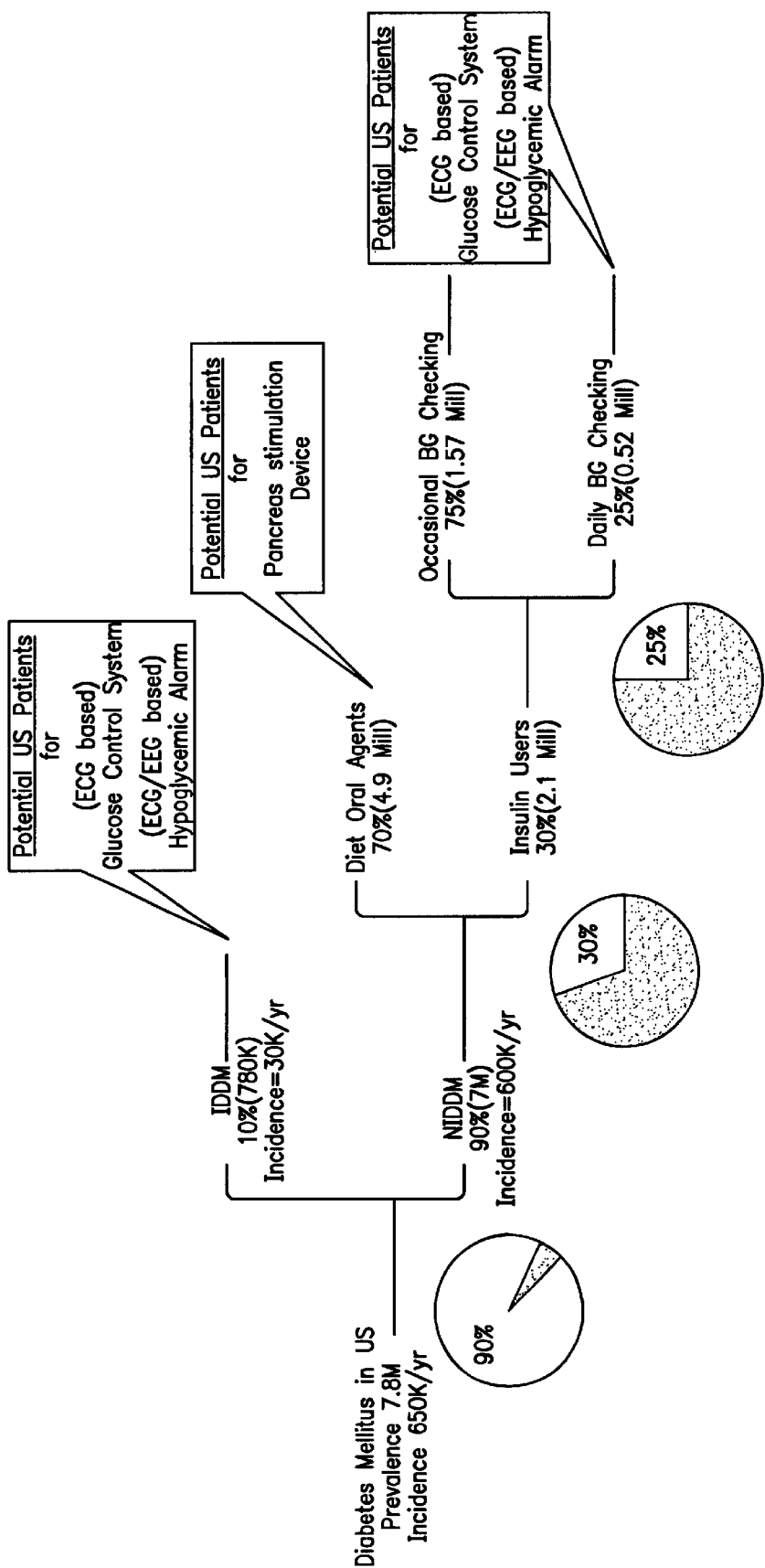
FIG. 1 shows the results of the Diabetes Control Project.

We confirmed that ECG changes correlate with blood glucose in non-diabetic subjects. Those changes result from the change in the blood potassium concentration due to insulin mediated cellular potassium uptake. In these subjects, we discovered a correlation between selected ECG parameters, notably QRS and T-wave mean and RMS parameters, and both plasma glucose and insulin. More particularly, we discovered that temporary hypokalemia induced by insulin mediated cellular potassium uptake often results in a reduction of T-wave amplitudes and a lengthening of ST segments. Those changes in waveform characteristics may be detected, for example, by looking for a shift in the frequency content of acquired ECG or electrogram signals (e.g., increased low frequency content). Hypokalemia has been discovered to prolong the duration of the cardiac action potential signal (see, for example, pp. 358–359 of Katz, supra). This situation applies to patients with non-insulin diabetes mellitus (NIDDM). However, for insulin dependent diabetes mellitus patients where insulin levels fall below a basal value, plasma glucose and ECG are not coupled. Rather, for these patients glucose uptake is not followed by a pancreatic insulin response, reflected in a substantially unchanged ECG following glucose uptake.

It has long been a problem to provide a glucose monitor or other type of monitor to indicate insulin need, which is capable of carrying out monitoring functions substantially continuously over long periods of time; does not require user activation or intervention; and can be miniaturized so as to either be worn externally or even implanted within a patient.

In contrast to prior art detectors, the basic approach to this problem as manifested in the subject invention has been to design a sensor utilizing both ECG and EEG signals, and to derive selected parameters from the ECG and the EEG which provide an accurate and reliable indication of insulin and blood glucose levels. Although there have been literature articles that disclose variations in ECG signals of diabetes in certain circumstances, there has been no disclosure or suggestion of a system using ECG signals in combination with EEG signals for continuous sensing of blood insulin and/or glucose, or such a system that could be worn by a patient or implanted.

As noted above, we discovered that insulin mediates both glucose and potassium cellular influx. The latter will induce hyperpolarization of the cell membrane, as well as ECG changes. We gathered data, which confirm that ECG changes do indeed occur in response to potassium cellular influx. We believe insulin-induced hyperpolarization of the cell and APD (action potential duration) prolongation are necessary steps for glucose transport. If this is indeed the case, the ECG may provide information regarding glucose transport. A mathematical model based sensor (software sensor) could be an option in that case for those episodes where insulin levels rises above critical levels enabling potassium uptake. This model requires patient-to-patient parameterization as well as adaptation if insulin sensitivity varies.

Electrocardiograms (i.e., ECGs or EKGs) may be employed to provide information on the state of ongoing glucose metabolic processes. Electrocardiographic changes have been described by Ostrander (Ostrander et al., 1964, Riley et al., 1972). It was discovered found that ST depression and T-wave changes of a sufficient degree do suggest heart disease in apparently normal individuals. Therefore, ingestion of glucose should be avoided before routine clinical ECG (Dear et al. 1969, Parrish et al. 1952). The R/T amplitude ratio has been reported to be sensitive to hypoglycemia (Heinemann, 1995).

As a start, the phenomenological approach has been chosen to test the hypothesis in a gross fashion. Eight healthy individuals were subjected to an oral glucose tolerance test (OGTT). An ECG was recorded while loading each individual with 75 grams of glucose immersed in 200 ml water. During the course of the experiment, blood samples where taken at a 10-minute interval for subsequent laboratory analysis of glucose, insulin and electrolytes. During the first 30 minutes of the experiment, a baseline ECG (using Holter Leads I,II,III) was recorded in the basal feeding state. The recorded ECG was then analyzed by accurate detection, classification, and averaging of all beats one minute prior to blood sampling. The beat average was then subjected to detection of ECG components.

All detected components were correlated with the laboratory glucose values obtained from the blood samples. T-wave related parameters showed significant correlation with blood glucose values. R and T-wave peak amplitude data were then entered into a linear regression model to predict glucose values. The correlation coefficient so obtained exceeded 75% in 6 out of 8 patients, which encouraged us to continue our investigations. During three subsequent experiments, we tested ECG sensitivity after administering 200 ml of glucose free water. No related ECG changes were observed.

Figure 2:
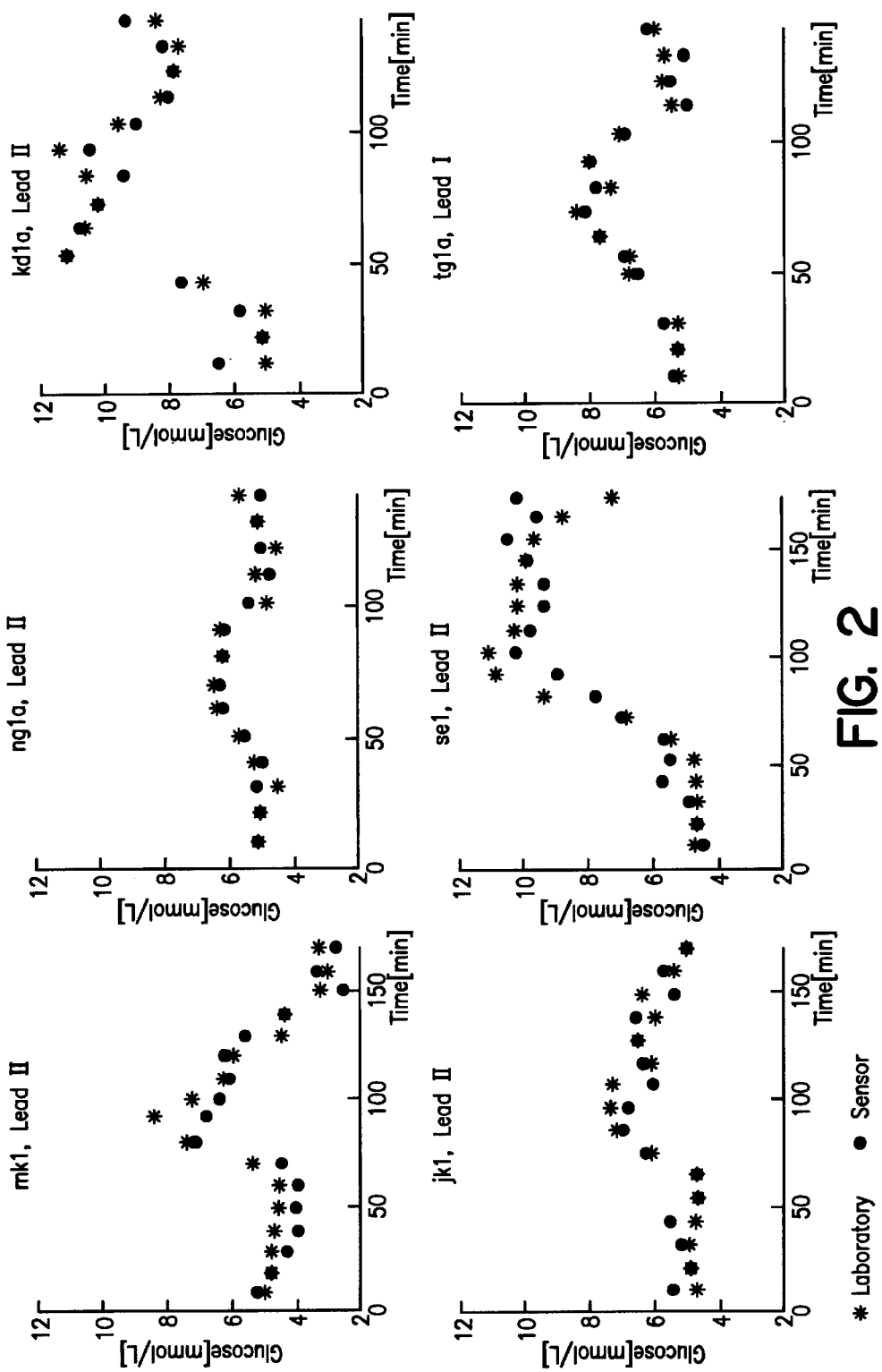
FIG. 2 shows selected quantitative blood glucose sensor data.

FIG. 2 illustrates the results of the foregoing experiments where correlation values exceeded 75%. Stars indicate laboratory values obtained from frequent blood sampling. Dots indicate ECG sensor values. The dashed lines indicate the time of oral glucose administration (either at 30 minute intervals or 60 minute intervals). Note that for subjects jk1, mk1 and se1 water with no glucose was administered at 30 minutes. This did not induce significant ECG changes.

Next, we began to address the mechanisms which might underlie the observed phenomena to support further specificity experiments, as well as to determine whether the observed effects were due to glucose, insulin or an interplay of both. The following hypotheses were developed: (1) ATP production might be sensitive to the amount of utilized glucose (see, for example, Teagtmayer, for example); (2) Elevated plasma insulin levels are known to induce increased sympathetic activity in response to carbohydrate intake and hypoglycemia. (see, for example, Berne et al. 1989, 1993, Spraul et al. 1994, Rowe et al. 1981 and Anderson et al. 1991, Kern et al. 1994); (3) Insulin mediated glucose transport is known to lower extracellular potassium due to potentiated net cellular influx. This so-called potassium co-transport is a clinical fact but the exact mechanism is not completely clear. Subsequent experiments were designed to address both mechanisms as insulin/glucose sensitivity questions.

The autonomic nervous system (ANS) influence on the observed effect was also tested by repeating our glucose administration experiments under sympathetic nervous system blockade. A cardioselective beta-blocker (metoprolol) was administered to each patient the night before the experiment and 30 minutes before the start of the experiment. No significant decrease in correlation was observed. Heart rate variations were reduced significantly, perhaps indicating beta-blockade. The ANS was therefore not further considered as the main mechanism driving the relation between glucose levels and ECGs.

In healthy individuals, the pancreas directly responds to elevated blood glucose levels by secretion of insulin. Blood glucose and insulin concentration profiles show grossly equivalent morphologies. To investigate exclusive action of either glucose or insulin, their respective working profiles have to be separated in time. This served as the basis of two experimental designs to reveal information on the primary initiator of observed ECG changes.

First, the hyperinsulinimic glucose clamp technique was used to elevate insulin levels while keeping glucose levels constant at a basal level. This requires intra-venous infusion of both insulin and glucose and frequent measurement of arterial glucose levels. Starting with low rate insulin infusion, peripheral glucose uptake is mediated which subsequently leads to decreasing glucose levels, which are immediately compensated by exogenous glucose infusion. This results in rising insulin levels while blood glucose concentration is maintained constant. Exclusive action of either glucose or insulin during the clamp experiment did not reveal any ECG changes. However, it must be noted that potassium infusion was required during the clamp experiment to prohibit low potassium levels.

Figure 3:
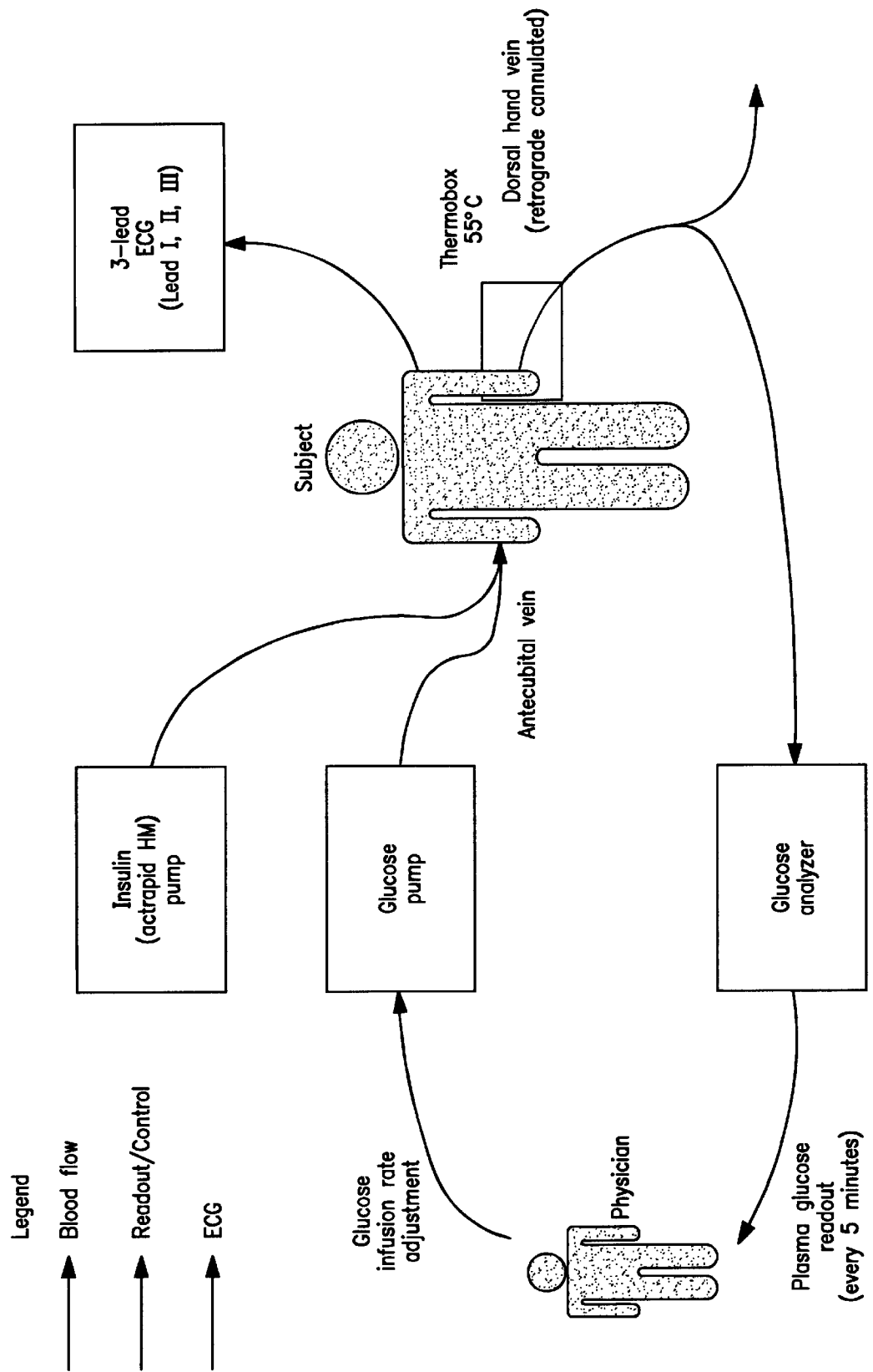
FIG. 3 shows a hyperinsulinemic glucose clamp setup.

FIG. 3 shows the hyperinsulinemic glucose clamp setup we employed. Blood glucose was measured by taking blood samples from the dorsal hand vein. Each hand was kept in a thermobox to enable arterialization of the venous blood. It should be noted that in those cases where the correlation coefficient exceeded 75%, T-wave amplitude decreased with increasing blood glucose values.

Second, a complementary experiment was designed to permit glucose levels to rise while keeping insulin concentrations at constant levels. This required an intra-venous glucose tolerance test (IVGTT) with IDDM patients having no endogenous insulin production. Glucose infusion was initiated and blood glucose levels were slowly elevated from basal to 16 mM. Within this period, no insulin was produced so that insulin concentrations were kept constant at basal levels obtained from subcutaneous resorption of previously injected long acting insulin. After reaching a peak, glucose levels were lowered by infusion of insulin until basal values were reached. In the first phase of the experiment, i.e. before the insulin peak was reached, exclusive glucose action was maintained. Next, while infusing insulin, both insulin and glucose became elevated and changed over time. During this phase, ECG changes were observed. The observed ECG effect was a result of insulin mediated uptake of glucose.

We conclude that both adequate insulin and glucose levels are required to obtain an ECG response. Quantitatively, the ECG measures the amount of utilized glucose mediated by insulin. The responsible glucose transporter (GLUT4) is available in muscle cells, including cardiac tissue. Mechanisms underlying the observed ECG effect have been studied and addressed in several studies. See, for example, Parrish et al. 1952 and Petersen et al. 1982. It has been discovered that that insulin mediates cellular uptake of glucose and potassium influx, although the precise role of potassium depletion remained unknown (see, for example, Rowe et al. 1980). If this indeed is the case, a link between potassium influx and plasma glucose removal is established.

Figure 4:
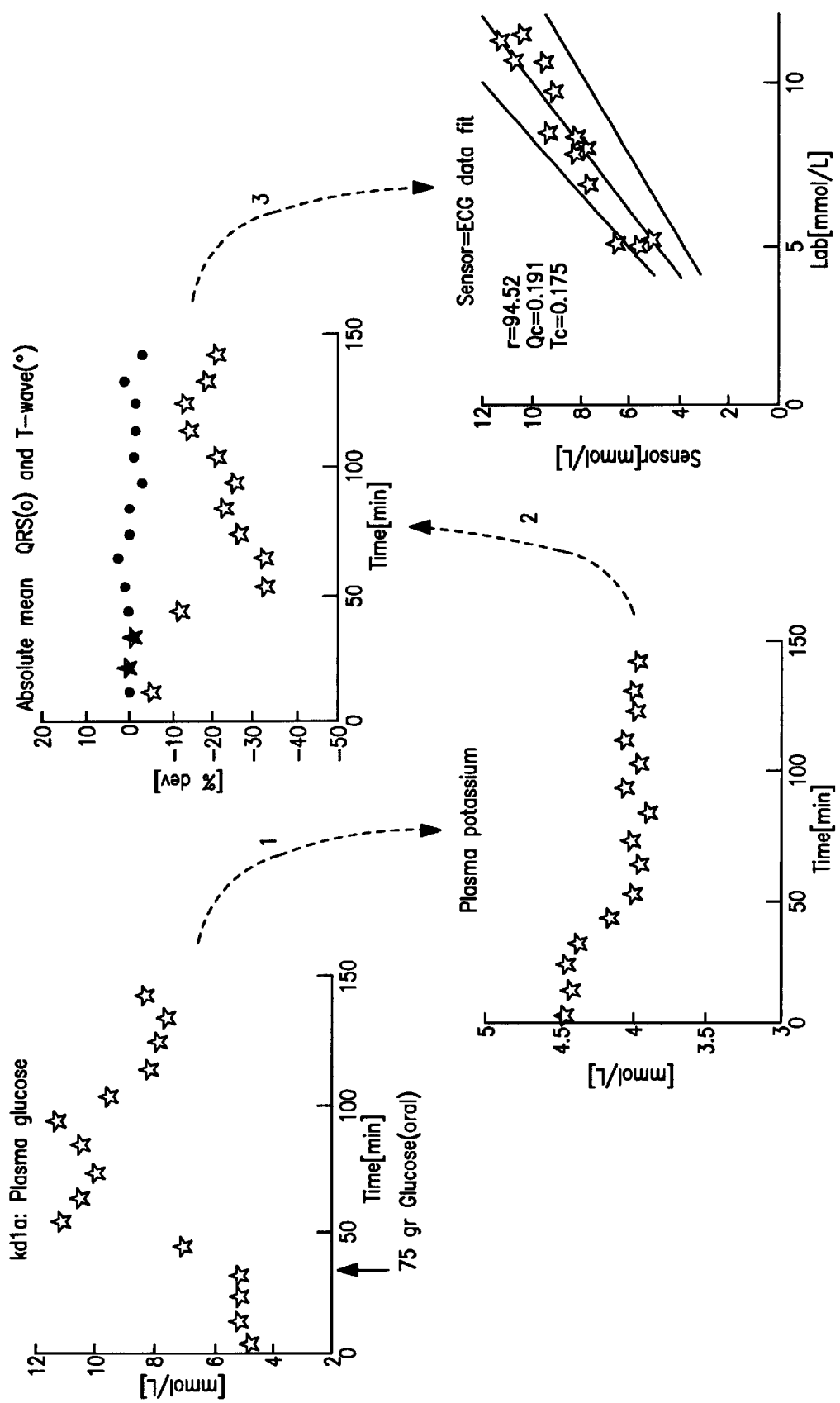
FIG. 4 shows correlations obtained between blood glucose levels and plasma potassium levels.

FIG. 4 shows changing extra-cellular potassium concentrations resulting from glucose challenge. At t=60 minutes, the glucose load rapidly increases blood glucose levels from basal levels to 11 mmol/L. Glucose was sampled at 10 min intervals (upper-left). Potassium levels decrease from 4.5 to 4 mEq/L, which could lead to the observed T-wave changes and subsequent correlation with blood glucose levels by means of cellular membrane hyperpolarization. The lower right graph shows ECG sensor vs. laboratory glucose values. Lines indicate +/−20% deviation.

Figure 5:
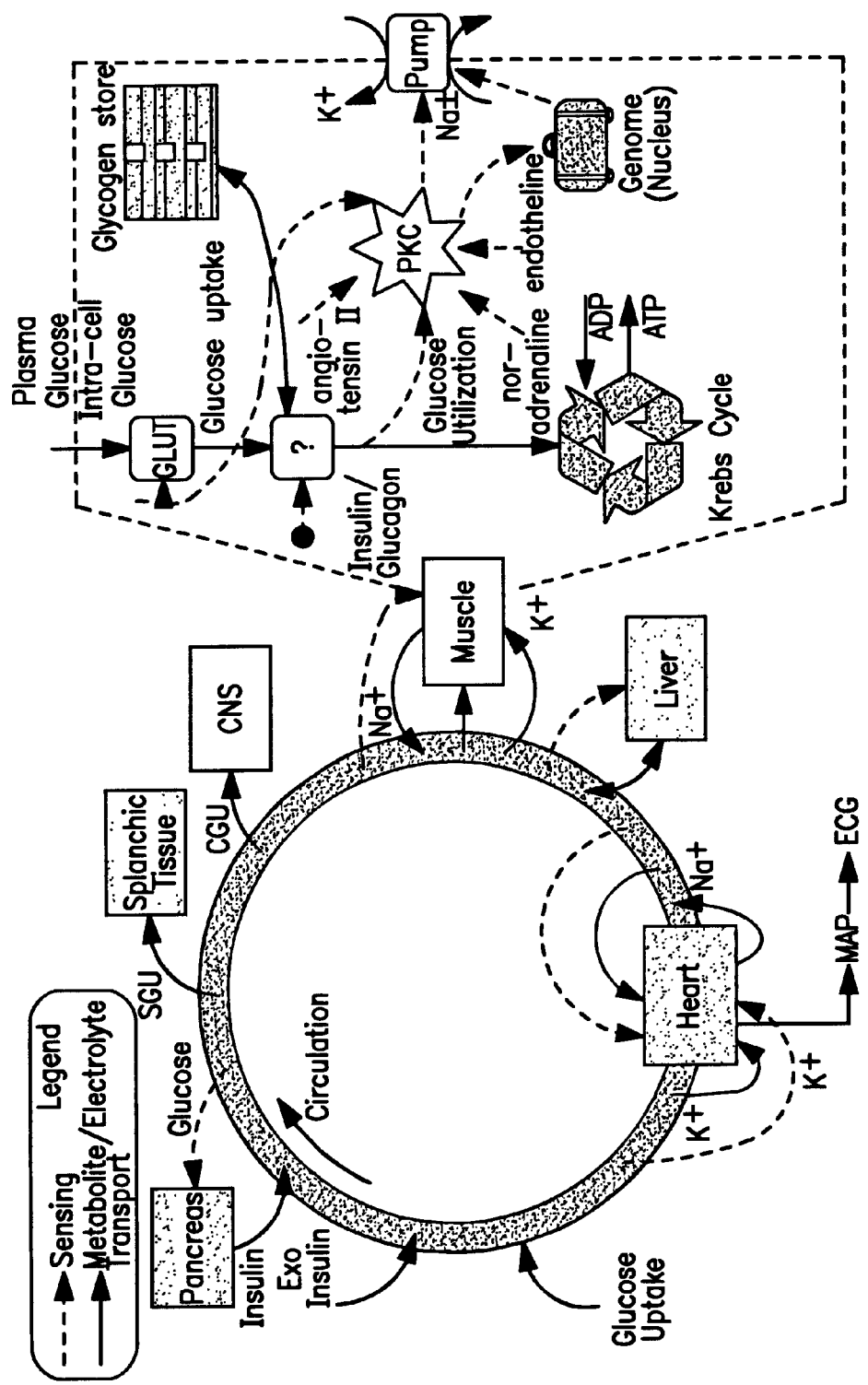
FIG. 5 shows an overview of glucose metabolism in the human body.

FIG. 5 shows an overview of glucose metabolism. Glucose uptake is sensed by the pancreas (dotted lines), causing insulin secretion (solid lines). The body structures, such as the liver and muscles, sense elevated insulin levels and respond by metabolizing blood glucose. This metabolism involves potassium . A detailed depiction of this metabolism for muscle tissue is shown. The relation of potassium "co-transport" is visualized for muscle tissue. Plasma glucose enters the cell mediated by insulin (GLUT4). The insulin/glucagon ratio determines whether glucose is utilized (glycolysis) or stored in glycogen (glycogenesis).

On the basis of our experiments and a detailed study of the metabolic processes at the (muscle) cellular level, we concluded that the ECG is sensitive to the utilization of blood glucose, i.e., insulin mediated uptake and glycolysis. The lack of a direct relation between blood glucose levels and insulin concentration in IDDM patients resulting from disturbed endogenous insulin production explains the lowered correlation between plasma glucose and ECG parameters observed in the study with IDDM patients. We postulate, however, that there exists an insulin dependent relation between cellular potassium uptake, which causes the ECG changes and leads to cellular glucose uptake. We also postulate that a relation between plasma glucose concentration and cellular glucose uptake exists such that may be possible to establish a mathematical model in which plasma glucose concentration is coupled to ECG changes.

Our ECG work, coupled with further EEG work described below, led us to the idea of a hypoglycemia alarm device, at least where IDDM patients undergo intensified insulin treatment. The sensor and alarm of the present invention are derived from our observation of insulin/glucose-induced ECG and EEG changes. In a non-diabetic subject, a glucose load introduced by, for example, food intake, leads to an increase in plasma glucose. In turn, the pancreas produces an increase in blood insulin. Following an increase in insulin, there is a cellular membrane change, which results in infusion of potassium into the cells, and a subsequent decrease in blood potassium along with glucose uptake. Lowered extracellular potassium or blood potassium levels shorten the cardiac monophasic action potential, and produce a steeper monophasic action potential upstroke. This, in turn, results in observable ECG and EEG changes, such as the development of U-waves, ST segment depression, shortening or other changes in the intervals of T waves, changes in QRS wave amplitudes and intervals, changes in Q-T and RR intervals and amplitudes, and small increases in R wave amplitudes.

Those changes, coupled with changes in EEGs occurring in response to the onset or development of hypoglycemia (e.g., changes from fast waves to slow waves in the brain), now permit us to identify the onset of hypoglycemic events sufficiently quickly that a beneficial agent may be delivered to the patient or the patient and/or a health care giver may be alerted before the patient slips into a state where he is himself unaware of the onset of hypoglycemia and in danger of slipping further into a hypoglycemic coma.

Figure 6:
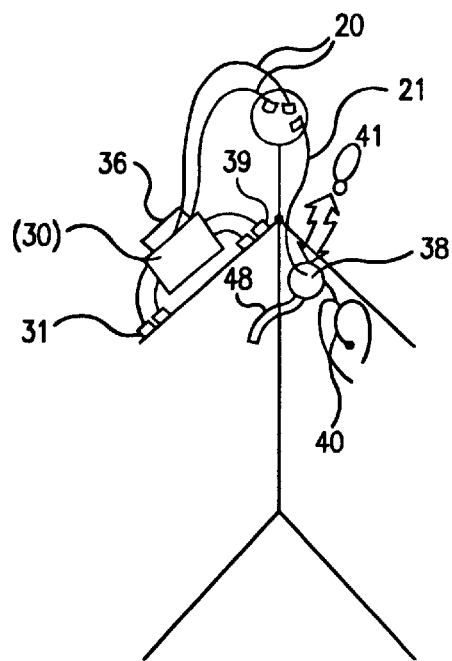
FIG. 6 is a schematic illustrating a patient with either a wearable pack or the like for carrying the system of the present invention, or an implanted embodiment of the system of the present invention.

Referring now to FIG. 6, there is shown a schematic representation of a patient with either a wearable pack 30 which houses a system in accordance with the present invention, or an implantable closed loop system apparatus 38 embodying the present invention. In the case of a wearable package 30, it is adapted to be attached to the patient at a convenient and medically optimal position. The package has connections to ECG electrodes 31 and EEG electrodes 20 for detecting the ECG and EEG in a known manner. The ECG and EEG electrodes may be conventional skin surface electrodes, subcutaneous electrodes, or intracardiac or intracranial electrodes.

Also shown schematically in FIG. 6 is a beneficial agent flow path 39, comprising a delivery tube or like means for controlled transport of a beneficial agent to the patient from a reservoir or other beneficial agent delivery device contained within housing 30. Further illustrated is input/output element 36, for inputting data to the system, as through a keyboard, and for displaying data.

Continuing to refer to FIG. 6, and in an implantable embodiment of the present invention, there is shown an implantable apparatus 38, having a lead 40 for insertion into the patient's heart to acquire intracardiac or epicardial ECG signals, lead 21 for insertion into or onto the patient's brain or skull to acquire intracranial or extracranial EEG signals, and a pump output 48. Note that either the wearable glucose monitor system or the implantable system suitably comprise a microprocessor and ECG and EEG signal processing hardware and software, as discussed in further detail below.

Either embodiment of the present invention may comprise many different combinations of hardware and software. The wearable system of the present invention may employ, for example, dedicated hardware for implementing appropriate signal processing algorithms. Combinations of implantable, subcutaneous, and external ECG and/or EEG electrodes may also be employed in various embodiments of the present invention. Optional patient input 23 may also be employed by the patient to provide inputs to processor 34 which train and teach processor 34 through reinforcement learning techniques to more accurately, reliably and quickly detect or determine the presence or onset of a hypoglycemic state in the patient.

Figure 8:
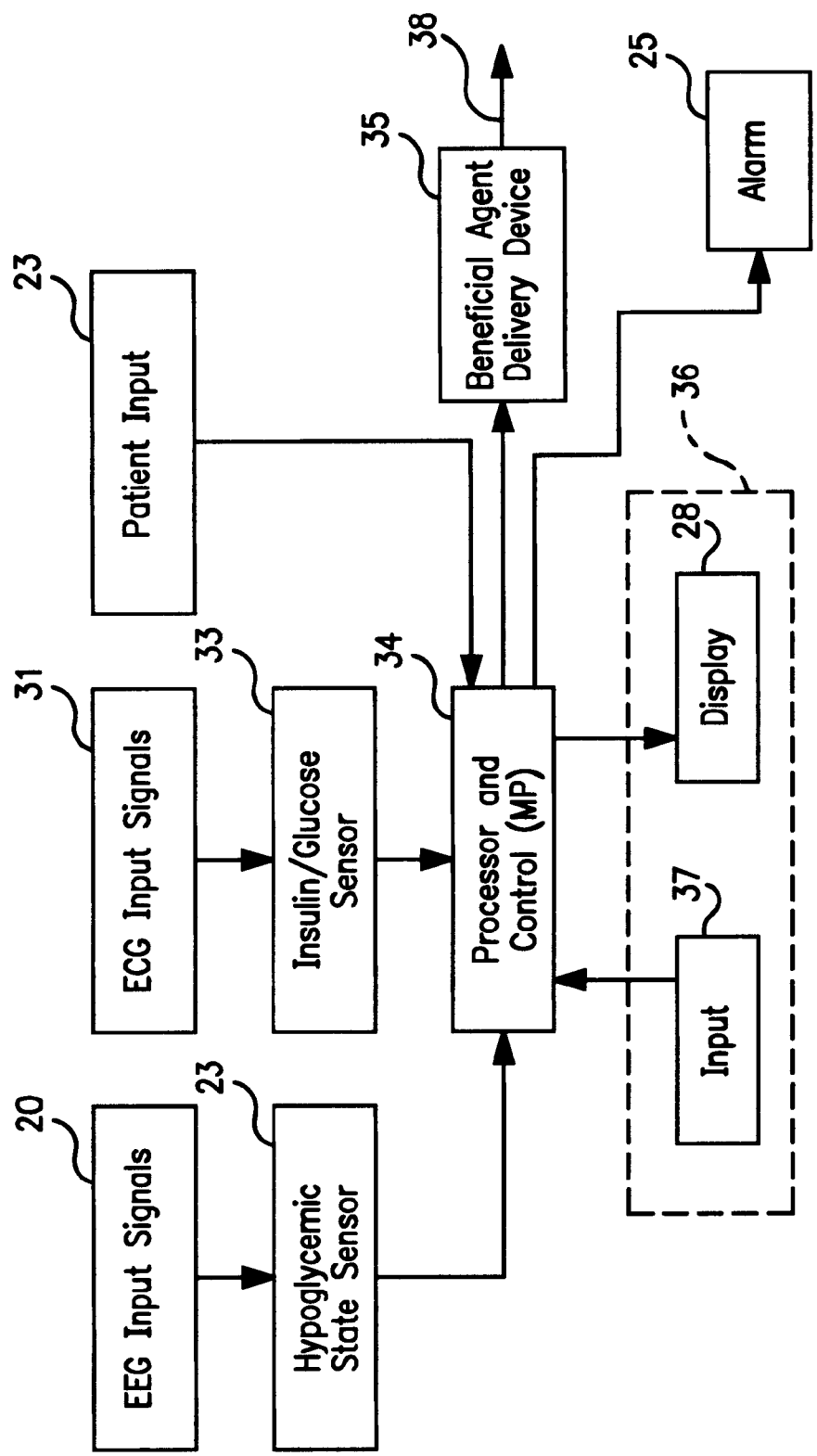
FIG. 8 is a block diagram of a wearable system utilizing the ECG-based and EEG-based sensors of the present invention.

Referring now to FIG. 8, there is shown a block diagram of an external, wearable embodiment of the system of this invention. As described above, a closed loop control system in accordance with this invention is directly controlled by continuous measurement of insulin or insulin and glucose concentration in the body, as well as EEG signals indicative of the presence or onset of hypoglycemia, and consists basically of insulin/glucose sensor 33, hypoglycemia sensor 23, insulin delivery pump 35, control 34, and input/output 36. Sensor 33 is described in detail below, and derives its input from ECG electrodes. Sensor 23 is also described in detail below, and derives its input from EEG electrodes most preferably emplaced at, in or near the frontal lobes of the patient's brain.

Beneficial agent delivery device 35 may provide a suitable beneficial agent to the patient through delivery catheter 38. When delivering insulin, for example, device 35 should be capable of delivering insulin with flow rates in the range of about 10–50 ul/min. Various types of insulin pumps are presently available as candidates for this system, as well as several forms of stable insulin in high concentration. It is, of course, desirable to have a capacity, which provides for extended refill periods. Device 35 is controlled by processor 34, which, as discussed above, suitably comprises a microprocessor and any desired combination of dedicated hardware and/or software.

Control block or processor 34 receives its primary inputs from sensors 23 and 33, and generates control signals for delivery of insulin or other beneficial agent as a function of, by way of example only, sensed or monitored insulin levels, glucose levels, insulin-mediated cellular glucose uptake, the onset or presence of hypoglycemia, the time rate of change of blood glucose or insulin levels, the state of blood glucose concentration indicated by the EEG signals, or any combination of the foregoing.

Control block or processor 34 may also be programmed and/or controlled through input 37, which may be a simple keyboard or other input elements suitable for the wearer to provide inputs such as, for example, when a meal has been ingested, or insulin has been taken. Display 28 may be provided by any suitable display and/or auditory means, by which the wearer can be informed of blood insulin and/or glucose level. Indeed, as a first simple embodiment, the wearable device may not incorporate controlled delivery of a beneficial agent such as insulin, but only provide blood constituent readings to the wearer.

Figure 7:
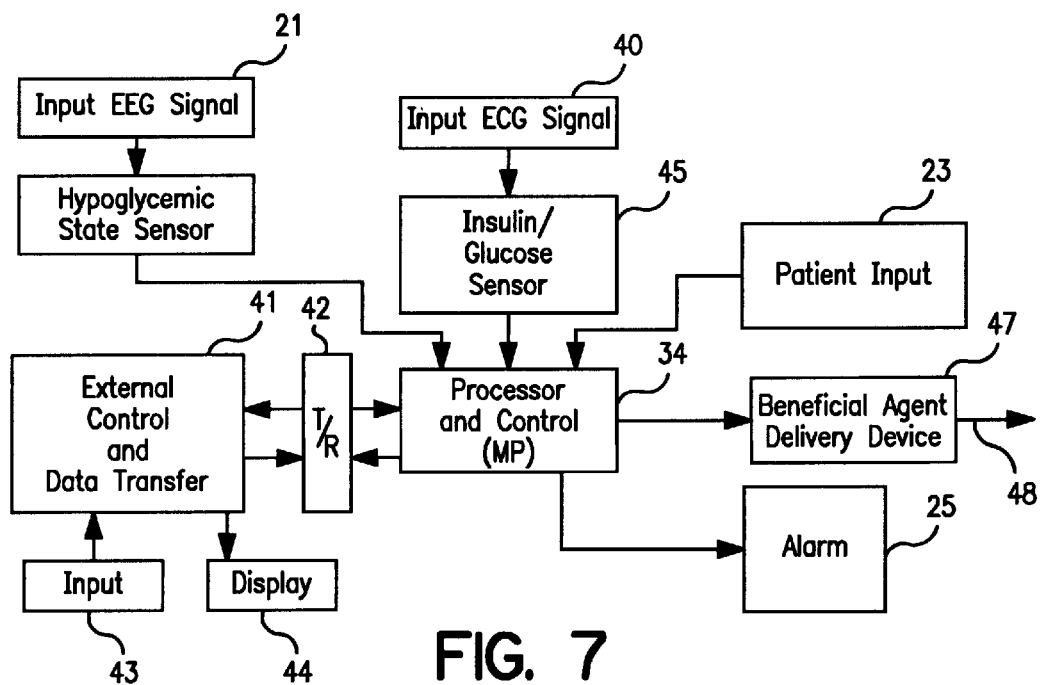
FIG. 7 is a block diagram of an implantable system utilizing the ECG-based and EEG-based sensors of the present invention.

FIG. 7 shows a block diagram of the primary components comprising one embodiment of a system of the present invention, which includes implantable apparatus 38. Implantable apparatus 38 incorporates the necessary housing, or container, such as known in the pacemaker art, for making the apparatus adaptable to being implanted in the patient (e.g., an hermetically sealed container which is biocompatible and biostable). Connected to the container are intracardial or epicardial lead 40 and intracranial, subcutaneous or extracranial lead 21. Leads 40 and 21 provide input signals, and may be similar to known pacing or intracranial medical electrical leads which sense patient intracardiac or epicardial and EEG signals in a known manner. Those signals are input into sensor 45, which is adapted to extract information from the ECG and EEG signals so as to sense insulin levels, glucose levels, insulin-mediated cellular glucose uptake, the onset or presence of hypoglycemia (as discussed in further detail below), or any combination of the foregoing.

The outputs of the two different sensors are transferred to processor and control block 34, which most preferably comprises a microprocessor, controller, computer, CPU or the like, and which processes the insulin, glucose and/or hypoglycemic state information to derive control signals for controlling beneficial agent delivery device 47, which may be, by way of example, an insulin delivery pump or a glucagen delivery pump. Device 47 provides its output through a catheter or other flow device 48. In an implantable embodiment where glucagen comprises the beneficial agent to be employed, it is desirable to have a glucagen capacity on the order of over 100 days, if not longer.

Implantable apparatus 38 also comprises transmit/receive block 42, which is in communication with external device 41. Element 41 provides for transfer of control and other programming data, by conventional electromagnetic means as utilized in the pacemaker art. Element 41 may also incorporate input 43, such as a standard dialing keyboard, for receiving input data from the patient or from a physician. Such data may be in the form of numerical data representative of amounts and time of glucose ingestion and/or insulin. The external apparatus also preferably comprises a display 44, such as a typical liquid crystal display, for outputting numeric and other information relating to sensed insulin level, or insulin and glucose level, as well as data indicative of extrapolated time for needing insulin and/or glucose intake.

It is to be noted that FIG. 7 shows a closed loop system. Such a system for insulin or other beneficial agent delivery may also be at least in part an open loop system in the respect that it may provide controlled insulin delivery solely as a function of input data concerning when the patient has ingested food, i.e., glucose intake. Also, in another embodiment of the present invention, the implantable apparatus is utilized only for deriving data concerning diabetes-related blood constituents to the external display, and therefore does not contain an insulin pump.

Note further that the embodiments of the present invention illustrated in FIGS. 7 and 8 may further include optional alarm 25. Alarm 25 may be triggered in response to processor and control 34 determining that a hypoglycemic event is imminent, or alternatively when the onset of a hypoglycemic event has already occurred. Alarm 25 may be an audible alarm, or may be a motion alarm which moves upon being activated such that the patient feels or otherwise senses the movement thereof and therefore is informed that a hypoglycemic event has been detected or is imminent. Alarm 25 may also be an audible alarm implanted near the patient's ear. It is also contemplated in the present invention that an alarm actuator and/or one or more EEG signal pre-amplifiers be emplaced on or within hollowed-out portions of the temporal bone.

Alternatively, in response to processor and control 34 determining that a hypoglycemic event is imminent or has already occurred, control 34 may route an alarm signal generated thereby through transmit/receive block 42 to external device 41. Device 41, in turn, may relay the alarm signal to an alarm device, or may itself display or sound an alarm in response to the receipt of the alarm signal. External device 41 may be include or be linked to a pager, a telephone, a computer or other communication device which can relay the alarm signal to an emergency service such as 911, a paramedic, a hospital, a physician, a neighbor or the like.

External device 41 may also be linked to or comprise a computer connected to the internet, the computer being capable of relaying the alarm signal via the internet to an appropriate server, telephone number (e.g., 911) or database where an appropriate response to the alarm may be generated (e.g., dispatch of an ambulance to the patient's address, telephone call of a physician or nurse to the patient's home, logging of alarm episode data in a database file, etc.).

Note further that the system of FIG. 7 may include optional patient input 23, which may be employed by the patient to provide inputs to processor 34 which train and teach processor 34 to more accurately, reliably and quickly detect or determine the presence or onset of a hypoglycemic state in the patient.

In the system of the present invention, it is specifically contemplated that the system have the capability to deliver more than one type of beneficial agent to a patient. For example, if the patient is diabetic and prone to episodes of hypoglycemia and hyperglycemia, then the system of the present invention may be configured to deliver, for example, glucagon, diazoxide or glucose during or just prior to a hypoglycemic event, as well as to deliver insulin or a sulfonylurea-based drug during a hyperglycemic event. Additionally, the system of the present invention is not limited to systems having the capability of detecting or sensing hypoglycemia, but includes within its scope systems having the capability of detecting or sensing hyperglycemia.

Figure 9:
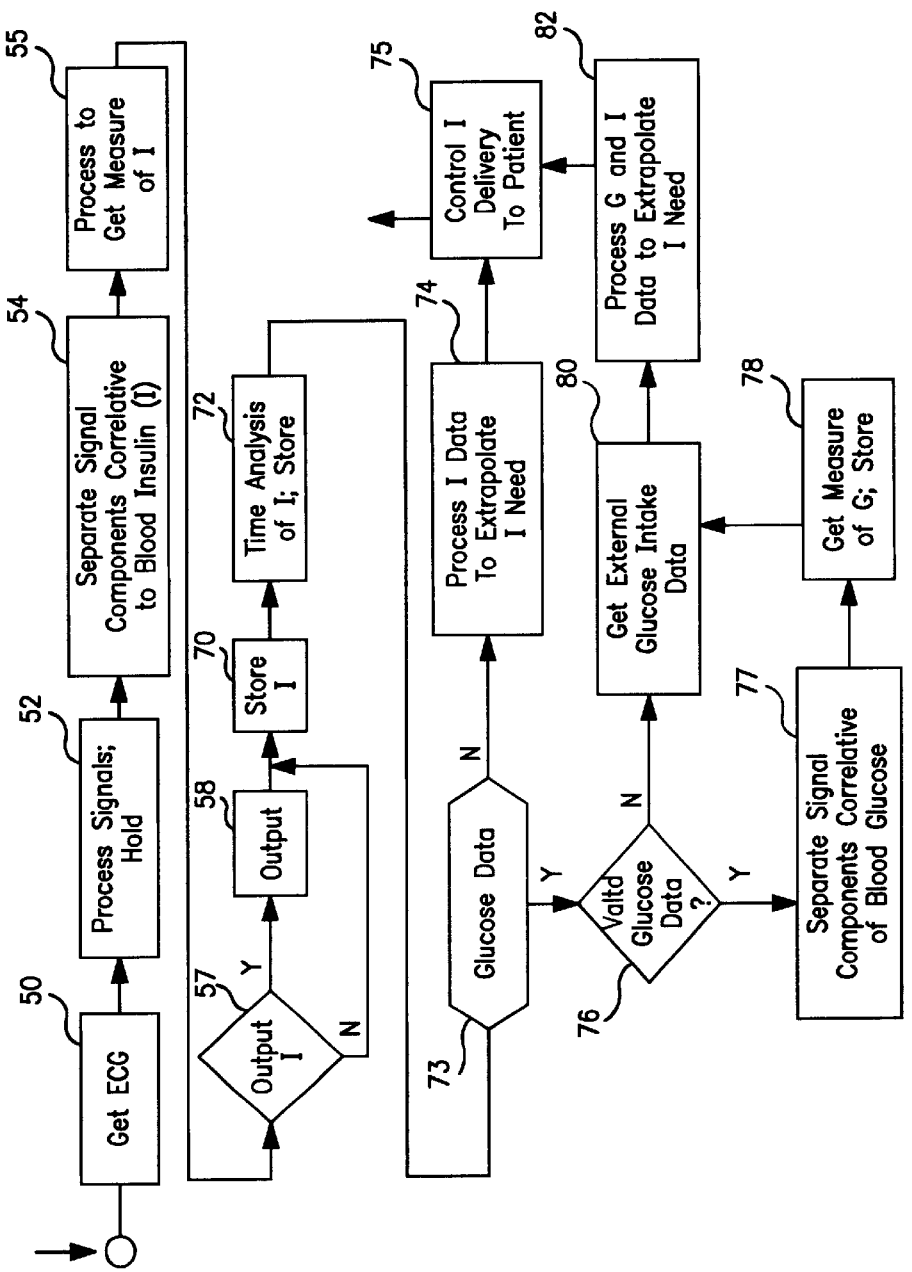
FIG. 9 is a flow diagram indicating the primary processing and control steps respecting ECG signal processing in one embodiment of a system and method of the present invention.

Referring now to FIG. 9, there is shown a flow diagram which is generally representative of the primary steps taken in either an external, wearable system, or in a system which comprises an implantable apparatus, as they relate to characterization of the sensed ECG or electrogram. EEG signal sensing and characterization/processing is described in detail further below. As described above, it is to be noted that either the wearable system or the implantable system may act simply as a sensor with an output indication and need not incorporate any form of controlled beneficial agent delivery. Thus, the scope of the invention may comprise all or just some of the steps and features set forth in FIGS. 7, 8 and 9. Further, it is to be noted that in a preferred embodiment of either the wearable system or the implantable system, many of the steps illustrated in FIG. 9, for example, are carried out under microprocessor control, and as such are steps executed by software loaded into or present in the hardware of the system.

At block 50, the system receives ECG signals, either surface ECG, or in systems having a lead extending into the patient's heart, intracardiac or epicardial ECG signals (i.e., electrograms). ECG signals may be averaged over a predetermined period of time such as, for example, ±1 minute, to enhance the signal-to-noise ratio of the sensed ECG signals. It is to be noted that the wearable device could, under certain temporary circumstances, be combined with a temporary lead to provide intracardiac signals. At block 52, the ECG signals are processed to verify sensing of actual patient beats, filter out extraneous signals, etc. The signal information is suitably transformed into digital form, and held in buffer memory. At 54, the signals are processed to separate out predetermined components, or parameters, that correlate blood insulin (I) and possibly also blood glucose (G). Those signal components or parameters include, but are not limited to, QRS and T wave amplitude and intervals, and Q-T and RR intervals.

As noted above, different signal components may exhibit different sensitivities, specificities or correlations with patient insulin and/or glucose data. Information concerning such sensitivities, specificities or correlations may be obtained by a physician through prior testing and then stored in the system for subsequent use in separating selected signal parameters. At block 55, the selected signal parameters are processed to get a measure of insulin. Steps 52, 54 and 55 are discussed in greater detail in connection with the flow diagram of FIG. 10.

Following obtaining a measure of blood insulin, at block 57 there is a determination as to whether to provide an output of the insulin level, i.e., provide an output at display 28 or 44. If yes, the output step is performed at block 58. The routine then proceeds to block 70, and stores the insulin data. At block 72, a time analysis of the insulin data is performed. For example, the time derivative of the data may be obtained and stored, as well as incremental changes occurring in insulin levels over predetermined time intervals such as, for example, preceding 15-minute, 30-minute and/or one-hour time periods.

At 73, it is determined whether the system is programmed to process glucose data, for example, and either sense or receive an input concerning patient glucose data. (Such an input may be, for example, an input based on the acquisition and processing of sensed EEG signals which may be employed to determine whether or not a hypoglycemic event has occurred, or if such an event is imminent, more about which we say below.) If no, meaning that the system is operating based only on insulin data, the insulin data is processed at 74 to extrapolate a patient insulin need. Note that, although not illustrated, the system may be adapted to receive an input from the patient concerning external injection of insulin, which data would also be used in processing future insulin need. The processing at 74 includes the time analysis data compiled at 72 in extrapolating insulin need. This extrapolated need is preformed cyclically and continuously, either every cardiac cycle, or periodically on the basis of batch data representative of a predetermined number of cardiac cycles. At 75, control of insulin delivery to the patient is performed, as a function of the control signals from block 74.

Returning now to 73, if the system is programmed to include glucose data, the next step, illustrated at 76, is to determine whether there is valid glucose signal data. As discussed above, the ECG data may or may not correlate to blood glucose level, depending upon the patient type and degree of diabetes. This validity determination may be programmed into the device, either the wearable or implantable device, so that the system is adaptable to consider the signal data for purposes of determining glucose only if validated by the physician. If the data is valid, at 77 the system separates out those predetermined signal components, which are correlative of blood glucose. Then, at 78, these components are processed to obtain a measure of blood glucose, which measure is stored. After this, or after no answer to the validity question at block 76, at 80 the system gets external glucose intake data, if there is any. Thus, if the patient has inputted information indicating a meal, data concerning the time of such meal, which represents glucose intake, is obtained from memory.

This glucose data, along with stored insulin data, is processed at 82 to extrapolate insulin need. This processing step is similar to that undertaken at 74, except that extrapolation of insulin need is performed as a function of both insulin and glucose data, or only glucose if the sensor is programmed to detect only glucose. The result of this processing is the generation of a control signal which is used to control insulin delivery, as shown at block 75.

Figure 10:
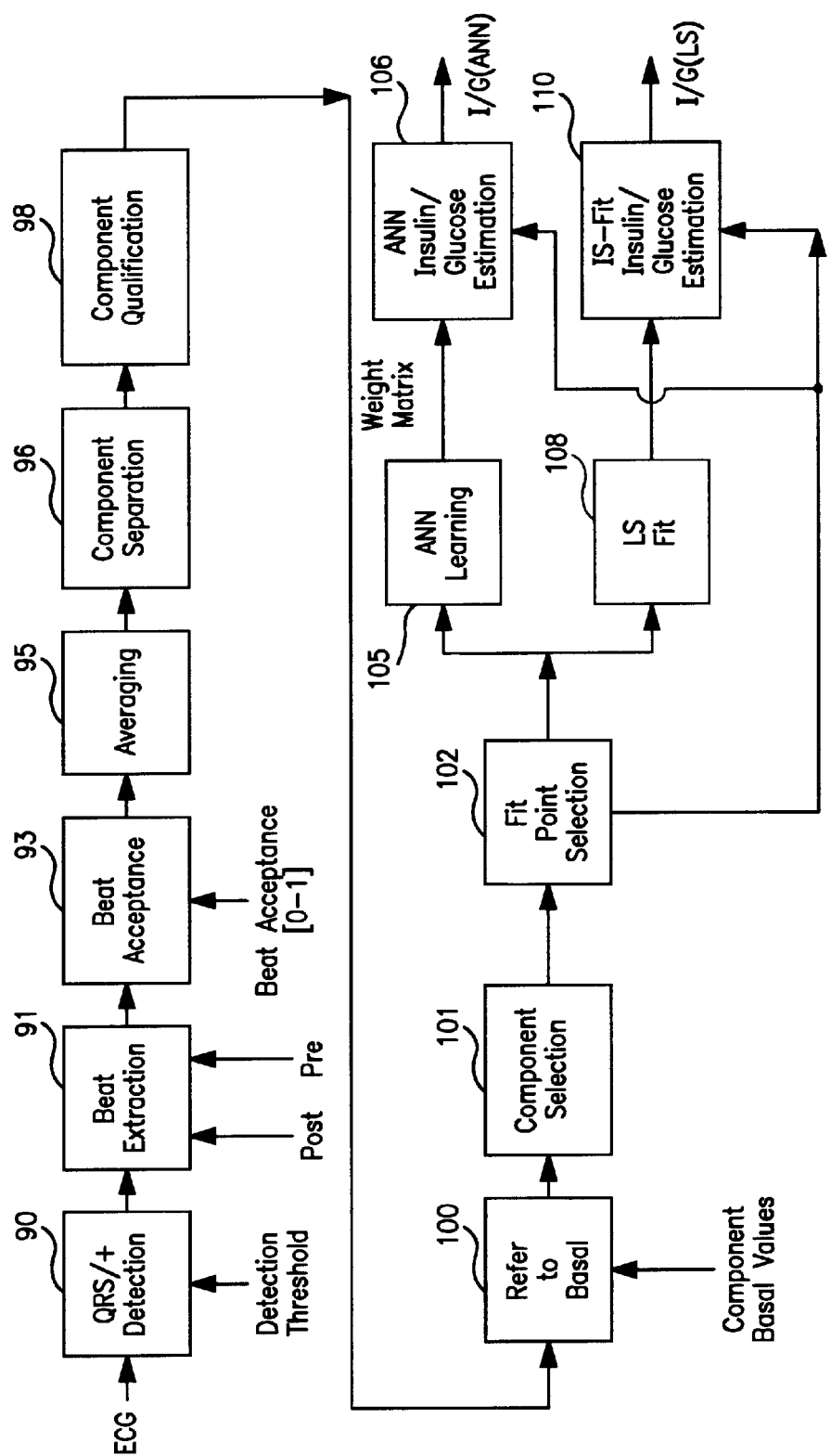
FIG. 10 is a flow diagram showing some steps taken in processing ECG signals to derive blood constituent data.

Referring now to FIG. 10, there is shown a block diagram representing the steps taken to process ECG signals to estimate cellular blood glucose uptake. Most of the steps are performed under software control, but are susceptible to an embodiment incorporating any degree of dedicated hardware and software. At block 90, the incoming signal is processed to reduce noise, electro-magnetic interference and baseline drift. Next, to detect QRS and/or T-wave components, the signal-velocity is compared to a detection threshold in order to detect the presence of one or more selected components, e.g., the QRS and/or the T wave component. Although the T wave may be included in the signal analysis, for purposes of discussion in connection with this portion of FIG. 10, the discussion is limited to QRS signal analysis.

Continuing to block 91, the step of beat extraction is indicated, based on "post" and "pre" timing signals to delineate the cardiac beat. These timing signals are calculated based upon a time window within which the signal QRS signal is expected to appear. The extracted signal is then analyzed at 93, as by comparing it to a standard waveform, and either accepted or not. Following this, at block 95 the cardiac beat characteristics are averaged. For example, the signal data may be averaged over a predetermined number of beats, such as 100, to avoid randomness and reduce respiratory modulation below acceptable limits thereby reducing false indications. Following this, at block 96, the signal is further separated into components or time stamps corresponding to each component, i.e., times stamps corresponding to various portions of the signal, such as the QRS start and end, T wave start and end, Q-T interval, RR interval, PQ interval, etc. Following this, at 98, the step of component quantification is undertaken, wherein the signal processing, preferably under microprocessor control, quantifies potential parameters such as QRS width; QRS absolute mean value; QRS RMS; T-wave absolute mean, T-wave RMS, T-wave maximum, T-wave width, QT interval, and/or RR interval.

At block 100, each quantified component or parameter is referenced to a basal value previously determined and inputted into the system. Following this, at 101 component selection is made. Thus, for determination of blood insulin level, in a presently preferred embodiment, QRS and T wave amplitudes are selected. At block 102, a fit point selection is made, for use in correlating the component or parameter data to the estimated insulin or glucose level. The component data can be analyzed either by an artificial neural network (ANN) approach, as shown at blocks 105 and 106, or by a least squares fit, as indicated at blocks 108 and 110.

As used herein, the term "ECG" encompasses the Vector Cardio Gram (VCG), which is an ECG-derived signal. As know in the art, a VCG signal is calculated from 3 orthogonal (x, y, z) ECG leads in a 3D plane or two ECG leads in a 2D plane, e.g., lead I and lead II. The VCG signal enables examination of the magnitude of the vector only, instead of both phase and magnitude, and thereby reduces the effects of cardiac movement or respiration. Processing ECG signals to obtain a VCG signal may be accomplished, for example, as part of the processing illustrated at 52.

It is specifically contemplated in the present invention that EEG data be acquired and processed in a manner similar to that described in "Biosignal-Veranderungen Wahrend Induzierter Hypoglykamien Bei Insulinpflichtigen Diabetikern", 1995, Georg Heger, Technical University of Vienna, Austria, PhD Thesis, and "Monitoring Set-Up for Selection of Parameters for Detection of Hypoglycaemia in Diabetic Patients", G. Heger et al., Medical and Biological Engineering and Computing, January, 1996, where EEG data were obtained using EEG Holter electrodes positioned near the frontal lobes of a patient's brain to provide a measure of patient blood glucose (BG) levels.

As described in Heger's thesis, supra, successive tomographic scans of the patient's brain at times 0 through 120

(corresponding to scans 1 through 25) show a strong correlation between blood glucose levels and the frequency content of the measured EEGs. That is, as blood glucose levels drop, higher frequency components of EEGs diminish in favor of lower frequency components as so-called slow waves begin to dominate electrical activity in at least the frontal portions of the brain. The presence of slow waves is generally considered characteristic of a hypoglycemic state in a patient. Thus, the electrical activity of the frontal lobe portions of the human brain has been discovered to provide at least an indirect measure of a patient's blood glucose level.

In human brain cells, there is no insulin-mediated uptake of glucose. Instead, glucose uptake occurs through a passive diffusion mechanism aided by the GLUT1 protein. The electrical response of the frontal lobes of the human brain to decreased blood glucose does not provide a means by which the actual or absolute blood glucose concentrations or levels of the patient may be determined, but instead provides a means of assessing whether or not a patient has entered a hypoglycemic state, and/or whether such an event is imminent. Thus, in combination with the ECG-derived estimates of blood glucose, insulin, the time rates of change of blood glucose or insulin, and the insulin-mediated cellular uptake of glucose described above, EEG signals provide a means of confirming or improving the accuracy of predicting the onset and/or presence of a hypoglycemic state.

The timing of state changes from euglycemia to hypoglycemia is favorable enough in most cases to permit a patient to be warned or alerted sufficiently early to undertake corrective action, such as, for example, the immediate intake of rapidly absorbable carbohydrates, self-administration of glucagon, and so on. Alternatively and/or additionally, a system of the present invention may be configured or programmed to automatically undertake corrective action by releasing rapidly absorbable carbohydrates or glucagon into the body of the patient in response to the detection of a hypoglycemic episode or the onset of same.

Figure 11:
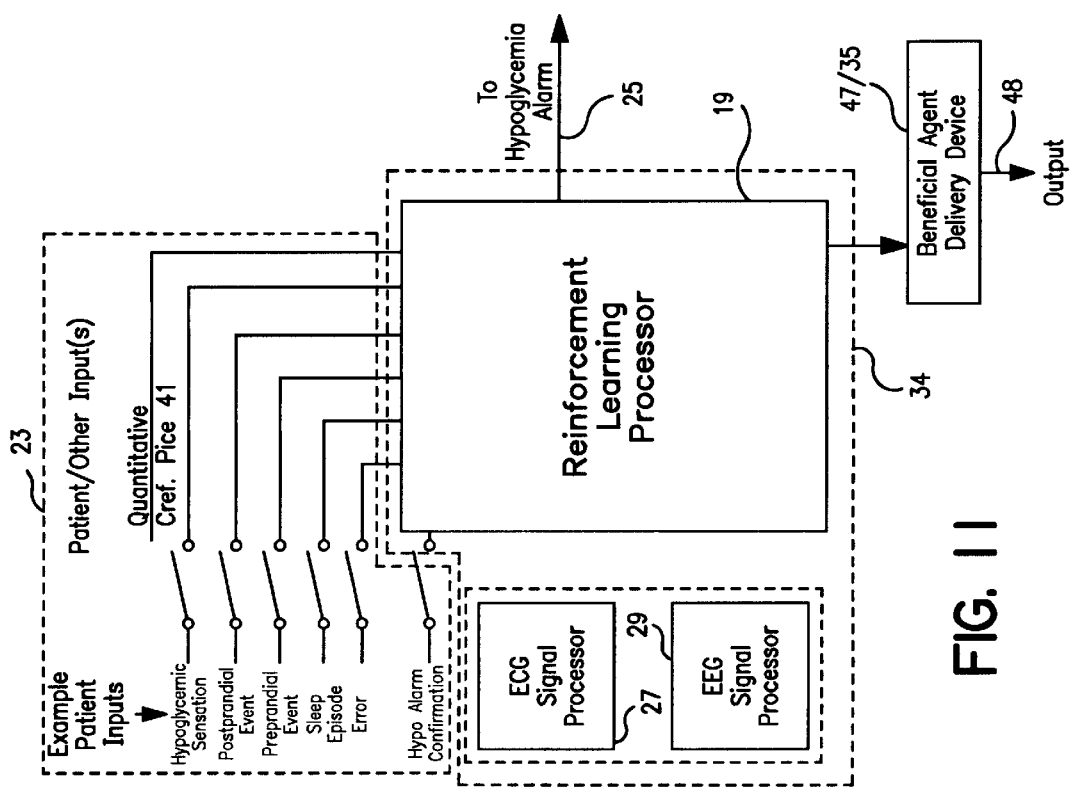
FIG. 11 shows a block diagram of one embodiment of a reinforcement learning processor of the present invention.

FIG. 11 shows a further embodiment of portions of a hypoglycemia alarm system of the present invention. The ECG signal processing block most preferably implements one or more algorithms to amplify and process one or more ECGs to detect, for example, insulin mediated glucose uptake. The EEG signal processing block most preferably implements one or more algorithms to amplify and process EEG signals for the purpose of detecting the onset or presence of slow waves. The hypoglycemia detection device may comprise two sensors: (a) an EEG sensor 21 or 20 indicative of a hypoglycemic episode or event (most preferably a forebrain sensor which is subcutaneous, intracranial or extracranial), and (b) ECG/electrogram sensor 31 or 40. Multiple processors and/or Digital Signal Processors (DSPs) may configured either in parallel or serial fashion to process the ECG and/or EEG signals in the Reinforcement Learning Processor.

Figure 12:
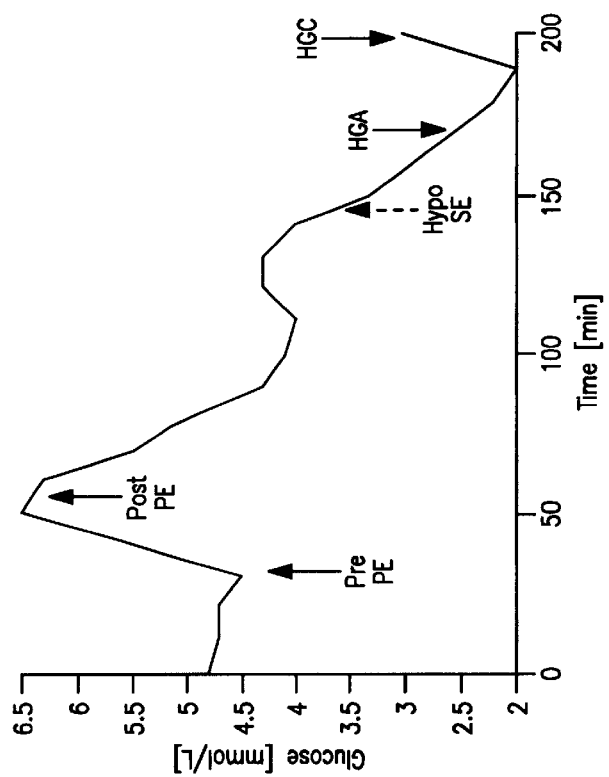
FIG. 12 shows a hypothetical blood glucose profile.

It will now be seen that the partial system illustrated in FIG. 12 is capable of sensing the concentration of diabetes-related blood constituents (such as the insulin mediated uptake of glucose), and then taking additional information concerning glucose dynamics to predict the manner in which a given hypoglycemic situation will evolve. Either one or both sensor inputs, in conjunction with processor 34 (which most preferably, but not necessarily, includes a reinforcement earning processor), may be employed to provide an alarm to the patient when blood glucose levels fall below predetermined critical or threshold values. Such an event can trigger the infusion of glucagon using an implantable or external infusion pump, notify an emergency health care service by dialing 911 through telemetric or other means, or take other predetermined action to signal an alarm.

In FIG. 11, the two different signal inputs, ECG input signals 31 and/or 40 and EEG input signals 20 and/or 21, are preferably pre-processed separately in ECG signal processor 27 and EEG signal processor 29 before being routed to reinforcement learning processor 19, although the same processor (e.g., a suitable microprocessor) may be employed to carry out all such functions. Digital signal processors (DSPs) may be employed to process EEG input signals 31 or 40 as well as EEG input signals 20 or 21. After pre-processing amplification, filtering and/or classification, the outputs of ECG signal processor 27 and EEG signal processor 29 are most preferably combined in reinforcement learning processor 28.

The basic principle under which reinforcement processor 19 operates may be described mathematically as follows:

$$G_{t+\Delta} = f(G_t, \Delta G),$$

where $G_{t+\Delta}$=patient's blood glucose or insulin level at time $t+\Delta$, $G_t$=estimate of patient's blood glucose or insulin level at time t, and $\Delta G$ =estimate of whether a hypoglycemic state is occurring or about to occur in the patient.

As discussed above, the estimate of $G_t$ is provided by processing the EEG, and the estimate of $\Delta G$ is provided by processing the ECG or electrogram. The quantity $G_{t+\Delta}$ is the output provided by reinforcement learning processor 19. In one embodiment of the present invention, when the quantity $G_{t+\Delta}$ reaches a predetermined threshold or level, alarm 25 is triggered and/or the delivery of a beneficial agent by device 47 is initiated. Alternatively, a series of quantities $G_{t+\Delta}$ may be stored in the memory of processor 19 and processed in respect of time to yield a time rate of range or slope of $G_{t+\Delta}$. The slope or other characteristics of stored values of $G_{t+\Delta}$ may in turn be employed to trigger alarm 25 or initiate device 47 when the characteristics reach a predetermined threshold or level.

Figure 14:
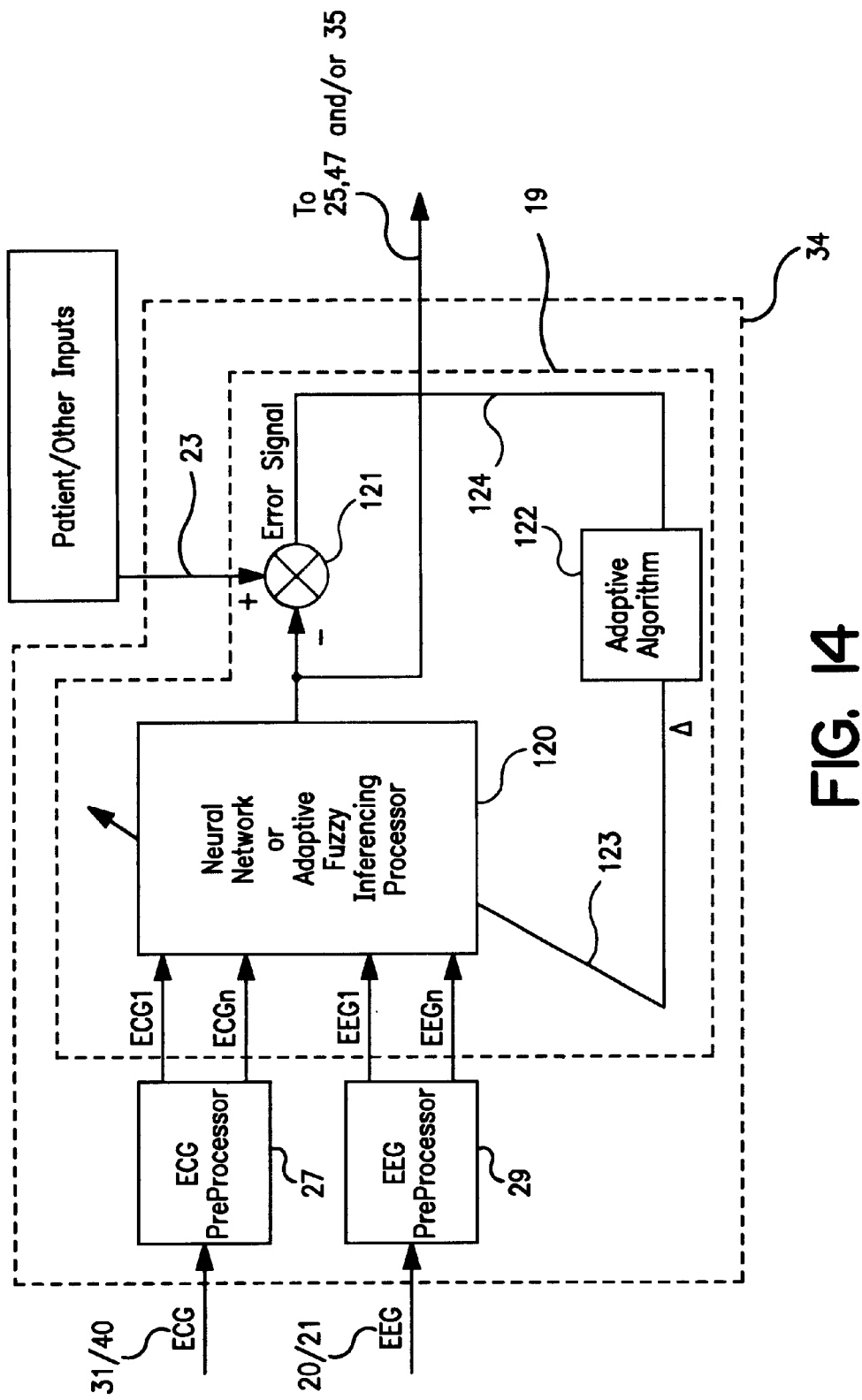
FIG. 14 shows one embodiment of processor 34 of FIG. 11.

A multi-dimensional data field defining acceptable and unacceptable EEG-derived parameters and ECG-derived parameters may be loaded into the memory of processor 34 and/or processor 19 to provide initial estimates of $G_{t+\Delta}$ for triggering and not triggering alarm 25 and/or delivery device 47 (see FIG. 14). Those initial estimates can be updated, refined and tuned to the particular patient who is employing the system of the present invention through the use of patient inputs to processor 19 (more about which we say below) and/or through the use well known data processing and filtering techniques for converging more quickly and accurately to desired solutions. The data field initially loaded into the system can be pre-tailored to the particular patient who will use it, or alternatively may be based upon cumulative, generalized patient population data.

The system illustrated in FIG. 11 also permits the patient, a health care giver and/or one or more sensors to input information concerning the patient's metabolic state through such means as direct electrical connection to the housing, telemetry, event buttons, and the like. Such a system is most preferably a learning system, where the patient's, health care giver's and/or sensor's inputs are employed to train and reinforce the learning system's ability to predict or determine the presence of a hypoglycemic event.

In one embodiment of the learning system of the present invention, the patient or health care giver confirms by any of a number various possible input means such as a keyboard, voice command, buttons, wires, actuation or de-actuation of magnetic or electrical fields, telemetry, and so on, that a particular event has occurred. Examples include the patient or health care giver confirming that a hypoglycemic sensation has been perceived (i.e., hypoglycemic sensation), that the patient has eaten (i.e., postprandial event), that the patient will soon eat (i.e., preprandial event), that the patient is going to sleep (i.e., sleep episode), that the hypoglycemic alarm signal output by the system was indeed correct (i.e., hypo alarm confirmation), that the patient has exercised or is about to exercise, or inputting any one or more of the patient's weight, the patient's medication type, the patient's medication dosage, the time at which the patient's medication (e.g., insulin) was administered, whether the drug was delivered orally, by injection, or an implantable infusion system, the patient's blood pressure, the patient's blood glucose or insulin levels, and so on. Sensor inputs to processor 34 may include, by way of example, the patient's blood pressure, blood glucose levels, blood insulin levels, epinephrine/ardrenalin levels, the patient's physical orientation (lying, standing, etc.), the patient's $HBa_{1c}$ (glycosylated hemoglobin) levels, the patient's instantaneous and/or cumulative (e.g., over the past 24, 48 or 72 hours) level of physical activity.

Continuing to refer to FIG. 11, event buttons the patient may press include the Hypoglycemic Sensation Event (Hypo-SE) button, which should be activated if the patient feels an upcoming hypo-glycemic attack. ECG/EEG signals preceding this event may be employed to teach the device that a hypoglycemic state is imminent. The PrePrandial Event (Pre-PE) button should be used indicate the start of food intake which precedes a period of about 30 minutes where it is unlikely that hypoglycemia will occur. Recorded signals in that time period can thus be employed as reference signals indicative of a non-hypoglycemic state in the patient. The PostPrandial Event (Post-PE) button may be pressed after finishing the intake of a substantial amount of food. The Confirmation of Hypoglycemia (HGC) button enables the patient to confirm or not to confirm (i.e., occurrence of a false positive) the alarm given by the system, or to inform the system that an alarm should have been given (i.e., occurrence of a false negative). Yet another button that may be used to indicate that the patient or a health care giver has delivered or administered insulin to the patient, thereby indicating an episode of increased risk of reactive hypoglycemia.

In another embodiment of the present invention, and as described above, input block 23 does not represent inputs entered under the control or direction of the patient or another person, but instead represents inputs based on physical measurements performed by one or more sensors connected to block 23 such as a blood glucose level sensor, a blood insulin level sensor, a blood potassium level sensor, a blood pressure sensor, a medication level or dosage sensor or indicator, an exercise sensor, an activity sensor, and so on.

As shown in FIG. 11, processor 34 most preferably comprises reinforcement learning processor 19. Such a processor 19 may comprise, for example, an artificial neural network (ANN) or any other suitable means such as a fuzzy logic processor, where the processor is capable of updating and improving its ability to characterize input signals, and capable of accurately and reliably characterizing those signals at or near the moment an event occurs so that the event may be accurately categorized as being indicative of heightened, normal or lowered blood glucose levels. Entering patient, health care giver or sensor-provided specific knowledge to the system leads to heightened alarm sensitivity and specificity owing to the feedback information provided thereto.

FIG. 12 shows hypothetical blood glucose profile. The profile is intended to be representative of blood glucose levels in a patient suffering from Type II DM, and shows variations in blood glucose occurring as a result of different events, such as the intake of glucose. Beginning at basal glucose levels between 4 and 5 mmol/L, ingestion of a meal (Pre-PE or pre-prandial event) brings glucose levels up to a maximum level (post-PE or post-prandial event) about 30 minutes after the intake of glucose. Within that time frame, insulin secretion begins to promote the uptake of glucose, which eventually reverses the blood glucose rate of change. In DM, patients sometimes suffer from severe post-prandial hypoglycemia, where blood glucose levels drop below basal levels.

Continuing to refer to FIG. 12, the term "Hypo SE" indicates a patient sensed hypoglycemic event. In response to Hypo SE, the patient, health care provider or sensor may provide the input "Hypoglycemic Sensation" to processor 34 as illustrated in FIG. 11. In FIG. 12, "HGA" means "hypoglycemic alarm", and indicates the point in time at which alarm 25 of FIG. 11 is provided with an alarm output signal by processor 34. In FIG. 12, "HGC" means "hypoglycemic alarm confirmation", and is yet another input provided to processor 34. In the event no "HGA" output is provided by processor 34, notwithstanding the fact that the patient has experienced a hypoglycemic event, then the input "HGE" (or hypoglycemic alarm error) may be provided to processor 34 (see input "Error" in FIG. 11) as a means of updating and correcting the erroneous estimate of a hypoglycemic event provided by processor 34.

A Sleep Episode button (SE event) may be employed to indicate the beginning of an overnight sleep episode. Alternatively, a respiration rate sensor, patient attitude or level sensor, EEG sensors, other suitable sensors, or any combination of the foregoing, may be employed to automatically indicate to the learning system that the patient has fallen asleep. It is important for the system of the present invention to have an accurate indication of whether or not the patient is sleeping because some DM patients are particularly vulnerable to the onset of hypoglycemia or even sudden death during sleep. This is because glucose released by the liver must be relied upon during sleep. Glucose release by the liver is regulated by glucagon, a counter-regulating pancreatic hormone to insulin (the secretion of which may be impaired in a diabetic patient). Thus, if a nocturnal hypoglycemic event should occur while a patient is sleeping, no counter-regulating action of glucagon may occur, and glycemic concentration may fall to life threatening values.

Figure 13:
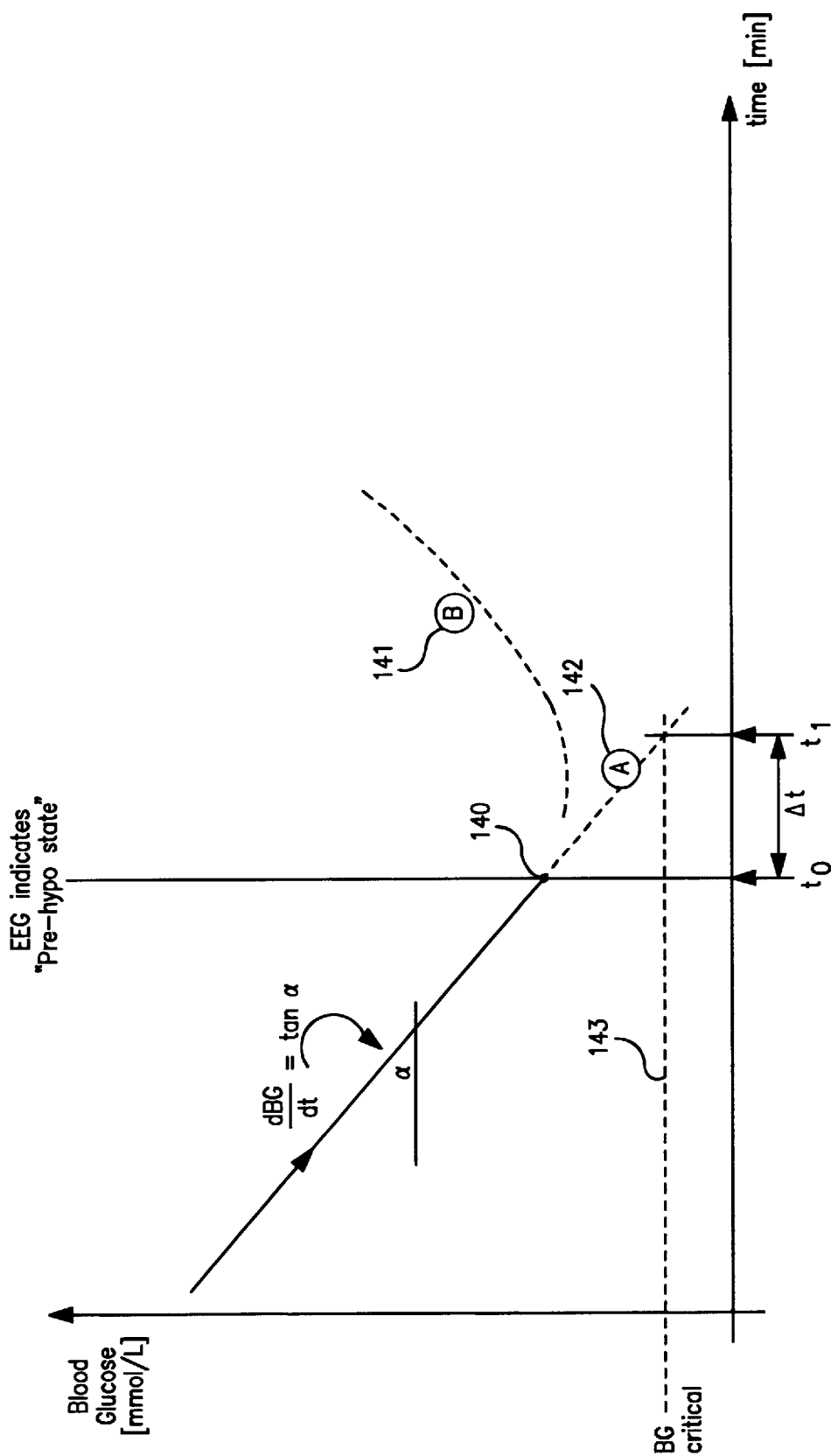
FIG. 13 shows another hypothetical blood glucose profile.

FIG. 13 shows another hypothetical blood glucose profile, where a patient's blood glucose level declines at a certain rate $dB_G/dt$ until processor 34 and one or more EEG signals indicate a pre-hypoglycemic state has developed in the patient at time $t_0$ (shown at 140 in FIG. 17). ECG signal inputs to processor 34 are next employed to determine and/or predict whether the patient's glycemic state has or will revert to a normal glycemic state (141 or "B") or instead has or will further deteriorate towards (142 or "A") or under a critical or undesired blood glucose level 143. In the present invention, output 25, 47 or 35 may be provided at time $t_0$ (which is defined or determined on the basis of EEG signals) instead of at time $t_1$ a period of time $\Delta t$ later (which in many patient prone to hypoglycemia may be 10–15 minutes). Thus, in the present invention the patient receives warning of an impending hypoglycemic state earlier than has otherwise been possible, and may also have a beneficial agent delivered to him earlier, either through the patient's own action while still conscious or through automatic delivery of same.

The system of the present invention is preferably configured to learn and update patient specifics such as the patient's insulin sensitivity. This, in turn, enables the system, for example, to determine and use quantitative blood glucose rate of change information ($dG_t/dt$) derived from the ECG in combination with EEG-indicated hypoglycemic event information. The combined information may then be employed to provide an early warning of an upcoming hypoglycemic event, and thereby permit the patient to prevent the onset of severe hypoglycemia (which can lead to coma, hospitalization or even death).

We believe the hypoglycemic alarm of the present invention is capable of providing enhanced control of diabetes, leading to a reduction in the chronic complications of DM by as much as 70% (as indicated by the Diabetes Control and Complications Trial or DCCT, 1993).

The DCCT study revealed that intensified insulin treatment decreased $HbA_{1c}$ levels by at least 2% and also subsequently reduced long-term microvascular complications by at least 70%, in comparison to standard treatment techniques. These favorable results were accomplished, however, at the cost of a twofold increase in mostly nocturnal hypoglycemic excursions, as well as increased incidence of hypoglycemic unawareness. The DCCT studies thus indicated that DM patients subjected to intensified insulin treatment were sub-optimally controlled. Later studies by Colwell (1994) and Wolffenbuttel (1995) provided similar results for NIDDM patients, where changes in medical care were found to be directly related to the improvement of $HbA_{1c}$ levels below 6% as a result of intensified insulin treatment. Nevertheless, and as discussed above, continuous detection of hypoglycemic threat remains an unmet clinical need. Optimal control of patients implies reducing the long term threats of microvascular complications and nocturnal hypoglycemic events. The system of the present invention satisfies those long felt but unmet needs by providing a reliable hypoglycemia detection system that permits enhanced, tight control of blood glucose levels, and thereby reduces the risk of hypoglycemic coma within acceptable limits.

The hypoglycemic alarm of the present invention may be implemented in either implantable or externally worn embodiments. In either case, an output alarm signal may be provided to a health care provider, emergency service, and/or directly to the patient, or may be employed to trigger the administration of insulin or glucagon (I/G), whether artificial or physiological. Many different types of warning signals may be provided by the system of the present invention, such as a warning signal to awaken the patient in the event nocturnal hypoglycemia is detected, or to initiate anti-hypoglycemic actions such as taking sugar, or the injection of glucagon or diazoxide when hyperinsulinemia is detected (see Joslin's Diabetes, pp. 65). Artificial administration of beneficial agents may be accomplished in any of several ways, such as by an I/G pump (whether mechanical, chemical, electrochemical, or acoustic), in-vivo stimulation of the patient's pancreas (see, for example, U.S. Pat. No. 5,919,216 entitled "System and Method for Enhancement of Glucose Production by Stimulation of Pancreatic Beta Cells").

Referring now to FIG. 11, and as discussed above, ECG input signals are particularly well adapted in the present invention for determining the rate at which blood glucose levels are changing (e.g., $dG_t/dt$). Such information by itself, however, is of limited value for persons with DM or highly athletic metabolisms, as the relationships between blood glucose levels and their corresponding rates of change in respect of time are no longer proportional or linear under such circumstances. Thus, in the present invention information from EEG signals and ECG signals is combined to overcome the deficiencies presented by looking to ECG signals alone as a means of predicting or detecting hypoglycemia. The system of the present invention may be further improved and reinforced by including inputs from the patient or health care provider.

As illustrated in FIG. 11, $dG_t/dt$ information derived from ECG inputs may be combined with information derived from EEC inputs to provide a more reliable prediction of the onset of a hypoglycemic event. For example, if information derived from EEG signals indicates that a hypoglycemic event is imminent, then processor 34 determine that may be output an alarm signal. If information derived from ECG inputs indicates that glucose uptake is occurring and information derived from EEG signals indicates a hypoglycemic event is imminent or underway, and taking into account insulin's half-life of approximately 6 minutes, processor 34 can predict that further lowering of blood glucose will occur and will therefore output an alarm signal. If information derived from ECG signals indicates that no further glucose uptake will occur or that metabolic equilibrium has been attained, and if information derived from EEG signals indicates no slow wave activity, then output of the alarm signal by processor 34 will be delayed or cancelled.

Examples of techniques that may be employed to process the ECG and EEG data input to processor 34 and to implement various embodiments of the learning system of the present invention may be found in: "Adaptive Signal Processing", Widrow et al., Prentice-Hall, New Jersey, 1985, ISBN 0-13-004029 01; "Neural Networks", Davalo and Naim, translated by A. Rawsthorne, MacMillan Education, London, 1991, ISBN 0-333-54996-1; "Neural Networks for Signal Processing", Kosko ed., Prentice Hall, New Jersey, 1992, ISBN 0-13-617390-X; "Neural Networks and Fuzzy Systems", Kosko, ed., Prentice Hall, New Jersey, 1991, ISBN 0-13-611435-0; "Fuzzy Control Systems", Kandel et al., CRC Press, Boca Raton, 1993, ISBN 0-8493-4496-4; "Neural Information Processing and VLSI", Sheu et al., Kluwer Academic Publishers, Boston, 1995, ISBN; "Wavelets in Medicine and Biology", Aldroubi and Unser, ed., CRC Press, Boca Raton, 1996, ISBN 0-8493-9483-X; "Wavelets and Their Applications", Ruskai et al., Jones and Bartlett Publishers, Boston, 1992, ISBN 0-86720-225-4; "Ten Lectures on Wavelets", Daubechies, 1992, Capital City Press, Montpelier, Vermont, 1992, ISBN 0-89871-274-2. Each of the foregoing publications is hereby incorporated by reference herein, each in its respective entirety.

FIG. 14 shows one embodiment of processor 34 of FIG. 11. Signals 31 and/or 40 and 20 and/or 21 are input into processor 34, preferably (although not necessarily) preprocessed by, for example, amplification, filtering, separation into various signal components (e.g., $ECG_1$ through $ECG_n$, and $EEG_1$ through $EEG_n$), and then routed to processor 19 for further processing.

As shown in FIG. 14, processor 19 may comprise, by way of example only, neural network or adaptive fuzzy inferencing processor 120, error signal processor 121 (which receives patient or other input 23), output 25, 47, and/or 35 and adaptive algorithm block 122 positioned in feedback loop 123 to neural network or adaptive fuzzy inferencing processor 120.

A decision boundary or surface is defined in processor 120 in an n-dimensional space, where n equals the number of inputs to processor 120. To one side of the boundary or surface, processor 120 determines that the inputs reflect a glycemic state falling within normal boundaries. To the other side of the boundary or surface, processor 120 determines that the inputs reflect a hypoglycemic and/or a hyperglycemic state. In response to the determination made by processor 120 as to where the inputs fall within the n-dimensional space, output 25, 47 and/or 35 is provided, and an error signal is produced at 121. Error signal processor 121 receives as an additional input(s) patient and/or other input 23. On the basis of the inputs to error signal processor 121, error output signal 124 is provided to adaptive algorithm block 122. In turn, adaptive algorithm block 122 produces output delta (or 123) which is employed to relocate, adjust, correct, and/or update the position of the decision boundary or surface stored in the memory of processor 120. In such a manner, the decision boundary or surface is continually adjusted and corrected to provide optimized indications and predictions of the patient's actual glycemic state.

FIG. 15(a) shows one neural network embodiment of processor 19 of the present invention. FIG. 15(a) shows a neural network embodiment of processor 120 of FIG. 14, where processor 120 comprises multiple layers of neural processors having weights stored therewithin corresponding to the n-dimensional decision boundary or surface described hereinabove. Weights $W_{ij}$ and $W_{kl}$, assigned to the various nodes located in the various layers are continually updates and changed in response to feedback signals $\Delta w_{ij}$ and $\Delta w_{kl}$ (or 123) provided by adaptive algorithm 122, which in turn, provides outputs on the basis of error output signal 124.

FIG. 15(b) shows one processing node of the neural network of FIG. 15(a). In the node, input weights $w_{i,1}$, $w_{i,2}$, and $w_{i,3}$ are first multiplied by inputs $i_1$, $i_2$ and $i_3$, respectively, the results are then summed and passed through a non-linear transfer function, as for example, a sigmoid or hard-limiting function. It will now become apparent to those skilled in the art, that many different embodiments of neural and/or adaptive processing techniques may be employed and fall within the scope of the present invention, even though they may not be described or shown explicitly herein.

Figure 16:
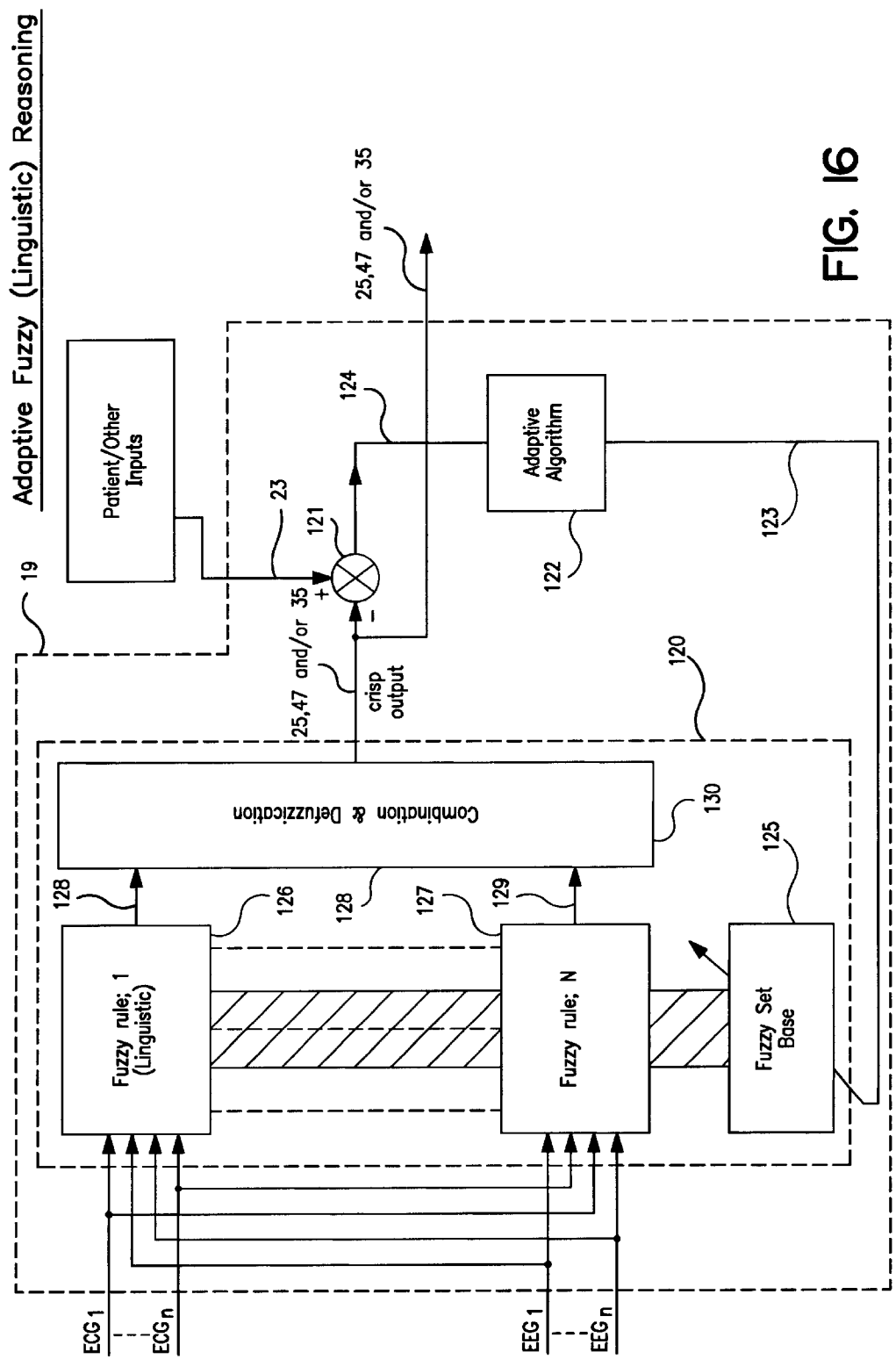
FIG. 16 shows one adaptive fuzzy (linguistic) reasoning embodiment of processor 19 of the present invention

FIG. 16 shows one adaptive fuzzy (linguistic) reasoning embodiment of processor 19 of the present invention. As shown in FIG. 16, processor 120 may comprise fuzzy rule processors 126 through 127, combination and defuzzification processor 128, adaptive algorithm processor 122, and fuzzy set base processor 125. Fuzzy set base processor stores and updates the fuzzy sets employed in fuzzy processors 126 through 127. Inputs ECG1 through ECGn and EEG1 through EEGn are input to fuzzy rule processors 126 through 127 where they may be fuzzified and passed through a plurality of fuzzy rule processors, each of which provides fuzzy outputs 128 through 129 to combination and defuzzification processor 130. Processor 130 provides a crisp output (e.g., yes or no, hypoglycemic or normal gylcemic state, hyperglycemic or normal glycemic state, etc.) to error signal processor 121, and also signifies output 25, 47 and/or 35. Error signal processor 121 generates output error signal 124 as an input to adaptive algorithm processor 122, which in turn generates updated outputs for input to fuzzy set base processor 125. Thus, the n-dimensional decision boundary or surface in this embodiment of the present invention is stored, updated and implemented in fuzzy processor 120. In such a manner, the decision boundary or surface is continually adjusted and corrected to provide optimized indications and predictions of the patient's actual glycemic state.

Although only a few exemplary embodiments of the present invention have been described in detail above, those skilled in the art will appreciate readily that many modifications are possible in the exemplary embodiments without materially departing from the novel teachings and advantages of the invention. Accordingly, all such modifications are intended to be included within the scope of the present invention as defined in the following claims. For example, processor 27, 29, 19 or 34 of the present invention may include any one or more of, but is not limited to, a CPU, a processor, a microprocessor, a controller, a microcontroller, an application specific integrated circuit (an ASIC), a digital signal processor (a DSP), a signal conditioning amplifier, pre-amplifier or filter, a micro-computer, a computer and the like. Processor 19 may be any processor capable of receiving at least first and second parameter data, analyzing same, and providing an appropriate response output, and thus is not limited to a learning processor or a reinforcement learning processor. Examples of appropriate processors 19 include, but are not limited to, CPUs, processors, microprocessors, controllers, microcontrollers, application specific integrated circuits (ASICs), digital signal processors (DSPs), computers and the like.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All patents, patent applications and printed publications disclosed hereinabove are hereby incorporated into the specification hereof, each in its respective entirety.

GLOSSARY

Clamp Shortcut for hyperinsulinimic glucose clamp.
Cumulative incidence rate Starting with a number of newborns, cumulatively applying age-specific incidence numbers for a certain disease on subsequent classes to yield a percentage of the newborns who will be affected by the disease.
Glycogenesis Under enzymatic control, glucose-6-phosphate is converted to glycogen (glycogen synthesis) in liver and muscle cells.
Glycolysis Chemical events, which lead to conversion of glucose-6-phosphate to puryvic acid, involved in continuing the carbohydrate metabolism (Krebs or citric acid cycle).
Glycogenolysis Under enzymatic and sympathetic nervous control (epinephrine and norepinephrine) glycogen is converted to glucose-6-phosphate ready to enter the blood-stream or glycolysis (glycogen breakdown).
Glyconeogenesis Synthesis of glucose by the liver from lactate, amino acids, glycerol etc.
Hypoglycemia Blood glucose level below 3 mmol/L. Glycemic state with increased danger developing hypoglycemic coma.
Hyperglycemia Blood glucose levels above about 15 (mmol/L glucose or 270 mg/dl glucose). Glycemic state with a danger of developing a hyperglycemic ketoacidosis.
Incidence rate New cases of a disease in a certain area during a time period (most 12 months) divided by the number of persons within the area [per 100,000 person years].
IVGTT Intra-Venous Glucose Tolerance Test. See OGTT, in this test, glucose is administered intra-venous.
Normoglycemic Glycemic levels within physiological bounds (i.e., 4–5 mmol/l glucose or 64–90 mg/dl glucose).

OGTT Oral Glucose Tolerance Test. Traditionally, 1 g glucose per Kg body weight is administered. In practice, 75 grams is frequently used.

Prevalence The proportion of persons who have a certain disease (e.g. diabetes type I) in a certain time period and place.

Specific incidence rate As Incidence rate, but now specified for a specific sub-population (e.g. age class).

We claim:

1. A system for at least one of predicting the onset of, and determining the presence of, hypoglycemia in a patient, comprising:
    an ECG sensor for obtaining signals representative of the patient's ECG;
    an EEG sensor for obtaining signals representative of the patient's EEG;
    first signal processing means for processing said ECG signals to provide first parameter data indicative of the patient's current blood insulin level;
    second signal processing means for processing said EEG signals to provide second parameter data indicative of the patient's future glucose level;
    means for providing a response to modify the patient's blood insulin level as a function of said first parameter data indicative of the patient's current blood insulin level and said second parameter data indicative of the patient's future glucose level.

2. The system of claim 1, wherein said response means comprises means for outputting an indication of the patient's blood insulin level.

3. The system of claim 1, wherein said response means comprises means for outputting an indication of the patient's glucose level.

4. The system of claim 1, wherein said response means comprises means for providing an alarm to at least one of the patient and a health care provider.

5. The system of claim 1, wherein said response means comprises means for delivering a beneficial agent to the patient.

6. The system of claim 1, wherein the means for response is a beneficial agent selected from the group consisting of glucagon, diazoxide, glucose, insulin, and a sulfonylurea-based drug.

7. The system of claim 1, wherein at least portions of the system are implantable.

8. The system of claim 1, wherein at least portions of said system are implantable in said patient and said response means comprises means for injecting a beneficial agent into said patient as a function of at least one of said first parameter data and said second parameter.

9. The system of claim 8, wherein said means for injecting a beneficial agent comprises a pump.

10. The system of claim 1, further comprising a wearable housing for housing at least portions of said system and adapted to be worn by a patient.

11. The system of claim 1, wherein said response means comprises output means for providing an output signal representative of the patient's insulin level.

12. The system of claim 1, wherein said response providing means further comprises means for analyzing said first and second parameter data.

13. The system of claim 12, wherein said response providing means further comprises additional response means for providing an additional response as a function of said analyzed first and second parameter data.

14. The system of claim 1, further comprising input means for inputting additional data.

15. The system of claim 14, wherein the input means is external.

16. The system of claim 14, wherein the additional data are representative of data selected from the group consisting of glucose intake data, insulin data, sleep episode data, hypoglycemic sensation data, post-prandial event data, and error data.

17. The system of claim 1, wherein the first signal processing means is incorporated into a device selected from the group consisting of a CPU, a processor, a microprocessor, a controller, a micro-controller, an ASIC, a DSP, a signal conditioning amplifier, pre-amplifier or filter, a micro-computer, and a computer.

18. The system of claim 1, wherein the second signal processing means is incorporated into a device selected from the group consisting of a CPU, a processor, a microprocessor, a controller, a micro-controller, an ASIC, a DSP, a signal conditioning amplifier, pre-amplifier or filter, a micro-computer, and a computer.

19. The system of claim 1, wherein the response providing means is incorporated into a device selected from the group consisting of a CPU, a processor, a microprocessor, a controller, a micro-controller, an ASIC, a DSP, a signal conditioning amplifier, pre-amplifier or filter, a micro-computer, and a computer.

20. The system of claim 1, wherein the response providing means comprises a device selected from the group consisting of a reinforcement learning processor, a neural network processor, an adaptive fuzzy logic processor, an adaptive processor, and an adaptive fuzzy inferencing processor.

21. The system of claim 1, further comprising storage means for storing patient blood insulin levels.

22. The system of claim 1, further comprising storage means for storing patient glucose levels.

23. The system of claim 1, wherein said response providing means further comprises extrapolation means for extrapolating anticipated time of insulin need as a function of said stored patient blood insulin levels.

24. The system of claim 1, further comprising means for processing said ECG signals and obtaining therefrom an indication of patient blood glucose.

25. The system of claim 1, wherein said response providing means further comprises delivery means for delivering insulin to the patient and control means for controlling said delivery means to provide indicated insulin in response to indicated patient insulin and glucose levels.

26. The system of claim 1 wherein the patient's future blood insulin level is estimated by analyzing the patient's ECG time rate of change.

27. The system of claim 26 wherein the patient's future blood insulin level improves accuracy in predicting the onset or presence of a hypoglycemic state.

28. A system for monitoring a glycemic state of a patient and controlling the glycemic state of the patient, comprising:
    an ECG sensor for obtaining signals representative of the patient's ECG;
    an EEG sensor for obtaining signals representative of the patient's EEG;
    first signal processing means for processing said ECG signals to provide first parameter data indicative of the patient's current blood insulin level;
    second signal processing means for processing said EEG signals to provide second parameter data indicative of the patient's future glucose level;
    means for providing a response to modify the patient's blood insulin level as a function of said first parameter data indicative of the patient's current blood insulin level and said second parameter data indicative of the patent's future glucose level.

29. The system of claim 28, wherein said response means comprises means for outputting an indication of the patient's blood insulin level.

30. The system of claim 28, wherein said response means comprises means for outputting an indication of the patient's glucose level.

31. The system of claim 28, wherein said response means comprises means for providing an alarm to at least one of the patient and a health care provider.

32. The system of claim 28, wherein said response means comprises means for delivering a beneficial agent to the patient.

33. The system of claim 28, wherein the means for response is a beneficial agent selected from the group consisting of glucagon, diazoxide, glucose, insulin, and a sulfonylurea-based drug.

34. The system of claim 28, wherein at least portions of the system are implantable.

35. The system of claim 28, wherein at least portions of said system are implantable in said patient and said response means comprises means for injecting a beneficial agent into said patient as a function of at least one of said first parameter data and said second parameter.

36. The system of claim 35, wherein said means for injecting a beneficial agent comprises a pump.

37. The system of claim 28, further comprising a wearable housing for housing at least portions of said system and adapted to be worn by a patient.

38. The system of claim 28, wherein said response means comprises output means for providing an output signal representative of the patient's insulin level.

39. The system of claim 28, wherein said response providing means further comprises means for analyzing said first and second parameter data.

40. The system of claim 39, wherein said response providing means further comprises additional response means for providing an additional response as a function of said analyzed first and second parameter data.

41. The system of claim 28, further comprising input means for inputting additional data.

42. The system of claim 41, wherein the input means is external.

43. The system of claim 41, wherein the additional data are representative of data selected from the group consisting of glucose intake data, insulin data, sleep episode data, hypoglycemic sensation data, post-prandial event data, and error data.

44. The system of claim 28, wherein the first signal processing means is incorporated into a device selected from the group consisting of a CPU, a processor, a microprocessor, a controller, a micro-controller, an ASIC, a DSP, a signal conditioning amplifier, pre-amplifier or filter, a micro-computer, and a computer.

45. The system of claim 28, wherein the second signal processing means is incorporated into a device selected from the group consisting of a CPU, a processor, a microprocessor, a controller, a micro-controller, an ASIC, a DSP, a signal conditioning amplifier, pre-amplifier or filter, a micro-computer, and a computer.

46. The system of claim 28, wherein the response providing means is incorporated into a device selected from the group consisting of a CPU, a processor, a microprocessor, a controller, a micro-controller, an ASIC, a DSP, a signal conditioning amplifier, pre-amplifier or filter, a micro-computer, and a computer.

47. The system of claim 28, wherein the response providing means comprises a device selected from the group consisting of a reinforcement learning processor, a neural network processor, an adaptive fuzzy logic processor, an adaptive processor, and an adaptive fuzzy inferencing processor.

48. The system of claim 28, further comprising storage means for storing patient blood insulin levels.

49. The system of claim 28, further comprising storage means for storing patient glucose levels.

50. The system of claim 28, wherein said response providing means further comprises extrapolation means for extrapolating anticipated time of insulin need as a function of said stored patient blood insulin levels.

51. The system of claim 28, further comprising means for processing said ECG signals and obtaining therefrom an indication of patient blood glucose.

52. The system of claim 28, wherein said response providing means further comprises delivery means for delivering insulin to the patient and control means for controlling said delivery means to provide indicated insulin in response to indicated patient insulin and glucose levels.

53. The system of claim 28 wherein the patient's future blood insulin level is estimated by analyzing the patient's ECG time rate of change.

54. The system of claim 53 wherein the patient's future blood insulin level improves accuracy in predicting the onset or presence of a hypoglycemic state.

55. A system for at least one of predicting the onset of, and determining the presence of, hypoglycemia in a patient, comprising:
    an ECG sensor for obtaining signals representative of the patient's ECG;
    an EEG sensor for obtaining signals representative of the patient's EEG;
    signal processing means for processing said ECG signals to provide first parameter data indicative of the patient's current blood insulin level and for processing said EEG signals to provide second parameter data indicative of the patient's future glucose level;
    means for providing a response to modify the patient's blood insulin level as a function of said first parameter data indicative of the patient's current blood insulin level and said second parameter data indicative of the patient's future glucose level.

56. The system of claim 55, wherein said response means comprises means for outputting an indication of the patient's blood insulin level.

57. The system of claim 55, wherein said response means comprises means for outputting an indication of the patient's glucose level.

58. The system of claim 55, wherein said response means comprises means for providing an alarm to at least one of the patient and a health care provider.

59. The system of claim 55, wherein said response means comprises means for delivering a beneficial agent to the patient.

60. The system of claim 55, wherein the means for response is a beneficial agent selected from the group consisting of glucagon, diazoxide, glucose, insulin, and a sulfonylurea-based drug.

61. The system of claim 55, wherein at least portions of the system are implantable.

62. The system of claim 55, wherein at least portions of said system are implantable in said patient and said response means comprises means for injecting a beneficial agent into said patient as a function of at least one of said first parameter data and said second parameter.

63. The system of claim 62, wherein said means for injecting a beneficial agent comprises a pump.

64. The system of claim 55, further comprising a wearable housing for housing at least portions of said system and adapted to be worn by a patient.

65. The system of claim 55, wherein said response means comprises output means for providing an output signal representative of the patient's insulin level.

66. The system of claim 55, wherein said response providing means further comprises means for analyzing said first and second parameter data.

67. The system of claim 66, wherein said response providing means further comprises additional response means for providing an additional response as a function of said analyzed first and second parameter data.

68. The system of claim 55, further comprising input means for inputting additional data.

69. The system of claim 68, wherein the input means is external.

70. The system of claim 68, wherein the additional data are representative of data selected from the group consisting of glucose intake data, insulin data, sleep episode data, hypoglycemic sensation data, post-prandial event data, and error data.

71. The system of claim 55, wherein the first signal processing means is incorporated into a device selected from the group consisting of a CPU, a processor, a microprocessor, a controller, a micro-controller, an ASIC, a DSP, a signal conditioning amplifier, pre-amplifier or filter, a micro-computer, and a computer.

72. The system of claim 55, wherein the signal processing means is incorporated into a device selected from the group consisting of a CPU, a processor, a microprocessor, a controller, a micro-controller, an ASIC, a DSP, a signal conditioning amplifier, pre-amplifier or filter, a micro-computer, and a computer.

73. The system of claim 55, wherein the response providing means is incorporated into a device selected from the group consisting of a CPU, a processor, a microprocessor, a controller, a micro-controller, an ASIC, a DSP, a signal conditioning amplifier, pre-amplifier or filter, a micro-computer, and a computer.

74. The system of claim 55, wherein the response providing means comprises a device selected from the group consisting of a reinforcement learning processor, a neural network processor, an adaptive fuzzy logic processor, an adaptive processor, and an adaptive fuzzy inferencing processor.

75. The system of claim 55, further comprising storage means for storing patient blood insulin levels.

76. The system of claim 55, further comprising storage means for storing patient glucose levels.

77. The system of claim 55, wherein said response providing means further comprises extrapolation means for extrapolating anticipated time of insulin need as a function of said stored patient blood insulin levels.

78. The system of claim 55, further comprising means for processing said ECG signals and obtaining therefrom an indication of patient blood glucose.

79. The system of claim 55, wherein said response providing means further comprises delivery means for delivering insulin to the patient and control means for controlling said delivery means to provide indicated insulin in response to indicated patient insulin and glucose levels.

80. The system of claim 55 wherein the patient's future blood insulin level is estimated by analyzing the patient's ECG time rate of change.

81. The system of claim 80 wherein the patient's future blood insulin level improves accuracy in predicting the onset or presence of a hypoglycemic state.

82. A system for determining insulin need of a diabetic patient, comprising
 ECG sensing means for sensing the patient's ECG and deriving therefrom an indication of patient current blood insulin level,
 EEG sensing means for sensing the patient's EEG and deriving therefrom an indication of patient future blood glucose level;
 processing means for determining at least one of patient insulin need and patient glucose need as a function of said indication of patient current blood insulin level and said indication of patient future blood glucose level, and
 response means for outputting an indication of at least one of said determined patient insulin need and said determined blood glucose need that includes both patent current need and patient future need.

83. The system of claim 82, wherein said ECG sensing means comprises first processing means for processing ECG signals and deriving therefrom selected parameter data.

84. The system of claim 83, wherein said ECG sensing means comprises second processing means for determining time variations of selected ECG parameters and for calculating anticipated insulin need as a function of said variations.

85. The system of claim 82, wherein said EEG sensing means comprises first processing means for processing EEG signals and deriving therefrom selected parameter data.

86. The system of claim 85, wherein said EEG sensing means comprises second processing means for determining time variations of selected EEG parameters and for calculating said anticipated insulin need as a function of said variations.

87. The system of claim 82, further comprising external data input means.

88. The system of claim 87, wherein said external data input means comprises time means for storing data representative of the time of patient glucose intake.

89. The system of claim 82, wherein said processing means comprises glucose variation means for calculating anticipated glucose variation as a function of said glucose blood levels, and wherein said response means comprises comparing means for comparing anticipated glucose variation with measured patient insulin level.

90. The system of claim 82, further comprising storage means for storing patient blood insulin levels.

91. The system of claim 82, wherein said processing means further comprises extrapolation means for extrapolating anticipated time of insulin need as a function of said stored patient blood insulin levels.

92. The system of claim 82, further comprising delivery means for delivering a insulin to the patient, and control means for controlling said delivery means to provide indicated insulin in response to indicated patient insulin and glucose.

93. The system of claim 82 wherein the patient's future blood insulin level is estimated by analyzing the patient's ECG time rate of change.

94. The system of claim 93 wherein the patient's future blood insulin level improves accuracy in predicting the onset or presence of a hypoglycemic state.

\* \* \* \* \*